US011905504B2

(12) United States Patent
Esch et al.

(10) Patent No.: US 11,905,504 B2
(45) Date of Patent: Feb. 20, 2024

(54) BODY CUBE AND PROCESS FOR CULTURING TISSUE

(71) Applicant: Government of the United States of America, as represented by the Secretary of Commerce, Gaithersburg, MD (US)

(72) Inventors: Mandy Brigitte Esch, Gaithersburg, MD (US); Longyi Chen, Gaithersburg, MD (US)

(73) Assignee: GOVERNMENT OF THE UNITED STATES OF AMERICA, AS REPRESENTED BY THE SECRETARY OF COMMERCE, Gaithersburg, MD (US)

(*) Notice: Subject to any disclaimer, the term of this patent is extended or adjusted under 35 U.S.C. 154(b) by 142 days.

(21) Appl. No.: 17/234,298

(22) Filed: Apr. 19, 2021

(65) Prior Publication Data

US 2021/0324312 A1 Oct. 21, 2021

Related U.S. Application Data

(60) Provisional application No. 63/011,794, filed on Apr. 17, 2020.

(51) Int. Cl.
*C12M 3/00* (2006.01)
*C12M 1/12* (2006.01)
*C12M 1/00* (2006.01)
*C12N 5/071* (2010.01)

(52) U.S. Cl.
CPC ............ *C12M 21/08* (2013.01); *C12M 25/06* (2013.01); *C12M 29/00* (2013.01); *C12N 5/0697* (2013.01)

(58) Field of Classification Search
None
See application file for complete search history.

(56) References Cited

U.S. PATENT DOCUMENTS

| 2006/0210451 A1* | 9/2006 | Anderson ............. B01L 3/5085 422/400 |
| 2018/0273888 A1 | 9/2018 | Esch |
| 2020/0070165 A1* | 3/2020 | Shuler .................... C12M 23/16 |

OTHER PUBLICATIONS

Norouzi et al., Orientation-based control of microfluidics) is directed to a system comprising a holder for holding a microfluidic chip in an orientation so as to control fluid flow on the chip, Mar. 7, 2016, PLoS One 11(3) (Year: 2016).*

* cited by examiner

*Primary Examiner* — Holly Kipouros
(74) *Attorney, Agent, or Firm* — Office of Chief Counsel for National Institute of Standards and Technology

(57) ABSTRACT

A body cube for culturing tissue that includes: an organ chip holder; and a body barrier chip and a first body organ chip disposed in the organ chip holder, the first body organ chip including a first cell culture chamber that receives cell culture medium and produces a first tissue in the first cell culture chamber, such that the organ chip holder receives cell culture medium and communicates the cell culture medium to the first cell culture chamber of the first body organ chip in response to rotation of the organ chip holder.

14 Claims, 23 Drawing Sheets

(A) 201

(B) 201

(A) 201

(B) 201

| organ | mean *in vivo* organ volume ± stdev. [L] | functional *in vivo* organ volume ± stdev. [L] | cube organ volume ± stdev. [μL] | square cube chamber area (with chamber depth = 200 μm) ± stdev. [mm$^2$] |
|---|---|---|---|---|
| GI tract | 1.23 ± 0.22 | 0.70 ± 0.13 | 9.6 ± 1.7 | 53.3 ± 9.5 |
| liver | 1.57 ± 0.26 | 0.94 ± 0.16 | 12.8 ± 2.1 | 71.1 ± 11.8 |
| kidney | 0.32 ± 0.07 | 0.19 ± 0.040 | 2.5 ± 0.53 | 13.9 ± 3.0 |
| bone marrow | 5.1 ± 0.89 | 2.98 ± 0.52 | 40.8 ± 7.1 | 226.7 ± 29.6 |
| blood | 5.82 ± 0.73 | 5.82 ± 0.73 | 79.7 ± 10.0 | N/A |

FIG. 15

| organ | $Q_{in\,vivo}$ ± stdev. [L/min] | $t_{phys}$ ± stdev. [min] | needed $Q_{cube}$ ± stdev. [µL/min] | simulated average $Q_{cube}$ ± stdev. [µL/min] |
|---|---|---|---|---|
| GI tract | 0.93 ± 0.16 | 0.75 ± 0.13 | 12.7 ± 2.2 | 11.0 ± 0.1 |
| liver | 1.30 ± 0.22 | 0.71 ± 0.12 | 18.1 ± 3.1 | 15.6 ± 0.1 |
| kidneys | 1.20 ± 0.25 | 0.16 ± 0.04 | 16.0 ± 3.3 | 13.8 ± 0.1 |
| bone marrow | 0.59 ± 0.10 | 5.05 ± 0.87 | 8.1 ± 1.4 | 7.0 ± 0.1 |

FIG. 16

|  | liver | bone marrow | GI tract | kidney |
|---|---|---|---|---|
| physiologic cell number per tissue chamber | $2{,}790 \times 10^3$ | $10{,}000 \times 10^3$ | $222 \times 10^3$ | $127 \times 10^3$ |
| number of seeded cells (percentage of physiological cell number) | $279 \times 10^3$ (10%) | $2{,}000 \times 10^3$ (20%) | $44.4 \times 10^3$ (20%) | $12.7 \times 10^3$ (10%) |

FIG. 19

|  | organ | calculated channel/chamber dimensions | | actual channel/chamber dimensions | |
|---|---|---|---|---|---|
|  |  | width [μm] | height [μm] | width [μm] | height [μm] |
| microfluidic channels | bone marrow | 80 | 150 | 75.7±2.2 | 149.1±3.8 |
|  | liver | 172 |  | 176.3±1.7 |  |
|  | kidney | 183 |  | 178.8±2.6 |  |
|  | GI tract | 143 |  | 147.3±2.9 |  |
| organ chambers | bone marrow | 15060 | 200 | 14859.3±41.3 | 207.9±4.6 |
|  | liver | 8430 |  | 8368.3±20.9 |  |
|  | kidney | 3730 |  | 3635.7±8.2 |  |
|  | GI tract | 7300 |  | 7247.9±18.3 |  |

FIG. 23

United States Patent No. US 11,905,504 B2

BODY CUBE AND PROCESS FOR CULTURING TISSUE

CROSS REFERENCE TO RELATED APPLICATIONS

The application claims priority to U.S. Provisional Patent Application Ser. No. 63/011,794 filed Apr. 17, 2020, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, MD, 20899; voice 301-975-2573; email tpo@nist.gov; reference NIST Docket Number 19-053US1.

BRIEF DESCRIPTION

Disclosed is a body cube for culturing tissue, the body cube comprising: an organ chip holder; and a body barrier chip and a first body organ chip disposed in the organ chip holder, the first body organ chip comprising a first cell culture chamber that receives cell culture medium and produces a first tissue in the first cell culture chamber, such that the organ chip holder receives cell culture medium and communicates the cell culture medium to the first cell culture chamber of the first body organ chip in response to rotation of the organ chip holder.

Disclosed is a body cube for culturing tissue, the body cube comprising: an organ chip holder comprising: an organ chip receiver bounded by a receiver wall and that: receives a plurality of body chips and a cell culture medium; and communicates to the body chips a volume of the cell culture medium that is limited to a near-physiological amount of the cell culture medium for growing tissue; a first cell culture medium reservoir bounded by a first reservoir wall and in fluid communication with the body chips and that receives the cell culture medium and communicates the cell culture medium to the body chips; a second cell culture medium reservoir bounded by a second reservoir wall and in fluid communication with the body chips and that receives the cell culture medium from the body chips in response to rotation of the organ chip holder; the body organ chips disposed in the organ chip receiver, such that that body organ chips are mechanically engaged by the receiver wall so that body chips rotate with the organ chip holder when the organ chip holder is subjected to rotation, and the body chips comprise: a first body organ chip comprising: a first body chip frame; a first fluid medium communication channel disposed in the first body chip frame and in fluid communication with the first cell culture medium reservoir, such that the first fluid medium communication channel receives the cell culture medium from the first cell culture medium reservoir and communicates the cell culture medium to a first cell culture chamber; the first cell culture chamber disposed in the first body chip frame and in fluid communication with the first fluid medium communication channel, such that the first cell culture chamber: receives the cell culture medium from the first fluid medium communication channel in response to rotation of the organ chip holder, such that a volume of the cell culture medium accommodated by the first cell culture chamber is limited to a near-physiological amount of the cell culture medium; produces a first tissue disposed in the first cell culture chamber; and provides contact between the first tissue and the cell culture medium; and communicates the cell culture medium to a second fluid medium communication channel; a second fluid medium communication channel disposed in the first body chip frame and in fluid communication with the first cell culture chamber and that receives the cell culture medium from the first cell culture chamber in response to rotation of the organ chip holder; a body barrier chip in mechanical engagement with the receiver wall and the first body organ chip by alignment member, the body barrier chip comprising: a body chip frame; an alignment member disposed in the body chip frame to mechanically engage the first body organ chip; and a cell culture chamber bounded by the body chip frame and opposing the first cell culture chamber of the first cell culture chamber, wherein the first tissue grows between the cell culture chamber of the body barrier chip and the first cell culture chamber of the first body organ chip.

Disclosed is a process for culturing tissue, the process comprising: receiving a cell culture medium in a first cell culture medium reservoir of a body cube; rotating the cell culture medium reservoir; communicating the cell culture medium from the first cell culture medium reservoir to a first fluid medium communication channel of a body organ chip in response to rotating the body cube, the body organ chip disposed in an organ chip receiver of an organ chip holder of the body cube; receiving, by the first fluid medium communication channel, the cell culture medium from the first cell culture medium reservoir; communicating the cell culture medium from the first fluid medium communication channel to a cell culture chamber of the body organ chip in response to rotating the body cube; receiving, by the first cell culture chamber, the cell culture medium from the first fluid medium communication channel; and growing tissue in the cell culture chamber in response to receiving the cell culture medium in the cell culture chamber to culture tissue.

BRIEF DESCRIPTION OF THE DRAWINGS

The following description cannot be considered limiting in any way. With reference to the accompanying drawings, like elements are numbered alike.

FIG. 15 shows average human organ sizes (based on a 70 kg body) and tissue culture chamber sizes;

FIG. 16 shows in vivo and in vitro flow rates and cell culture medium residence times for the four tissues co-cultured in the body cube;

FIG. 19 shows physiological cell number for $73000^{th}$ of human tissue, and cell number per cell culture chamber seeded into the co-culture cube according to the Example;

FIG. 23 shows calculated and actual sizes of channel and chamber dimensions according to the Example. Measured values represent means obtained from 4 devices±standard deviations.

DETAILED DESCRIPTION

A detailed description of one or more embodiments is presented herein by way of exemplification and not limitation.

It has been discovered that a body cube herein cultures tissue using a flow of culture medium provided either by a pump, or by rotation of the body cube such that the flow of the culture medium is determined by gravity. The body cube is microphysiological article that includes body chips disposed in an organ chip holder that can be operated with a near-physiological amount of a blood surrogate.

Advantageously, the body cube can culture multiple tissues with near-physiological amounts of blood surrogate. Conventional microphysiological systems cannot operate with a near-physiological amount of liquid. Conventional devices can use 10 to 200 times as much liquid than would be physiological. The body cube overcomes this issue and uses near-physiological amounts of blood surrogate through three-dimensional (3D) integration and low-volume reservoirs that reduce a length of interconnecting fluidic channels and that provide device volumes filled with liquid. In a presence of too much liquid, i.e., greater than near-physiological amount, results of drug testing experiments with conventional devices can be unreliable because toxic metabolites are diluted in-situ. This presents a problem when conventional devices are used to predict the efficacy or toxicity of drugs since both depend on drug metabolite concentrations. Conventional systems that contain too much liquid may not be able to predict drug action in the human body. The body cube solves this issue and provides more reliable test results, wherein the body cube minimizes the volume of interconnecting fluidic channels and provides near-physiological blood surrogate levels that overcomes the reliance of conventional multi-organ microphysiological systems on containing many times (10 to 200 times) as much liquid than is physiological.

The body cube cultures tissue as a pumpless multi-organ microphysiological system that can be operated by gravity to drive fluidic flow of near-physiological amounts of blood surrogate as a modular device that can have independent organ chips to mimic the human body. The body cube can reduce the liquid volume by, instead of using a two-dimensional (2D) array of tissue growth chambers, a 3D architecture of body organ chips arrange cell culture chambers to grow tissue stacked on one another, forming a cube of tissues. This configuration provides short interconnecting channels that include small fluid medium communication channels that are fluid vias in the body cube that connect the cell culture chambers similar to connections inside the human body. This design significantly reduces the amount of liquid needed to operate the body cube to culture tissue than conventional devices.

Figure 1:
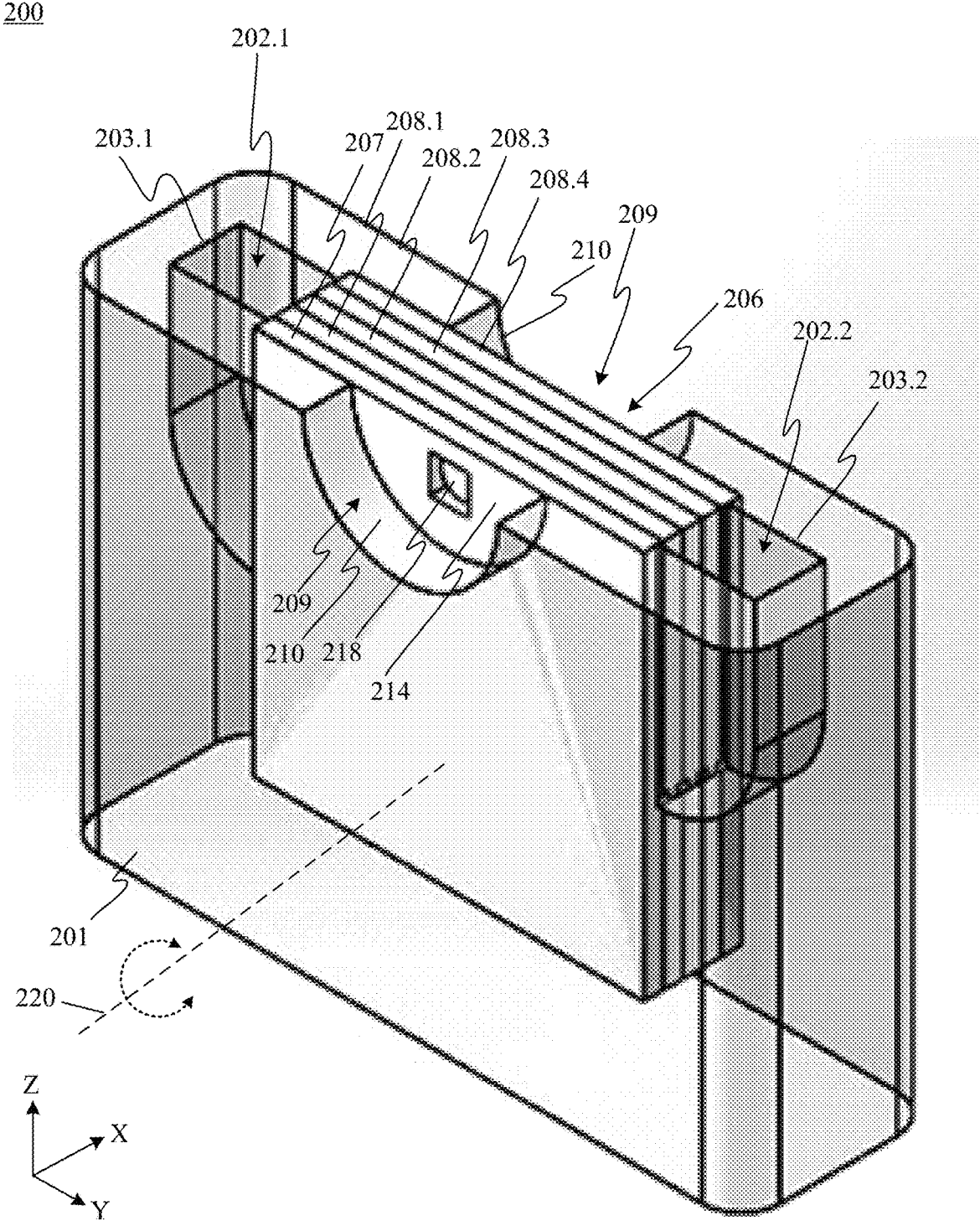
FIG. 1 shows a perspective view of a body cube.
Figure 2:
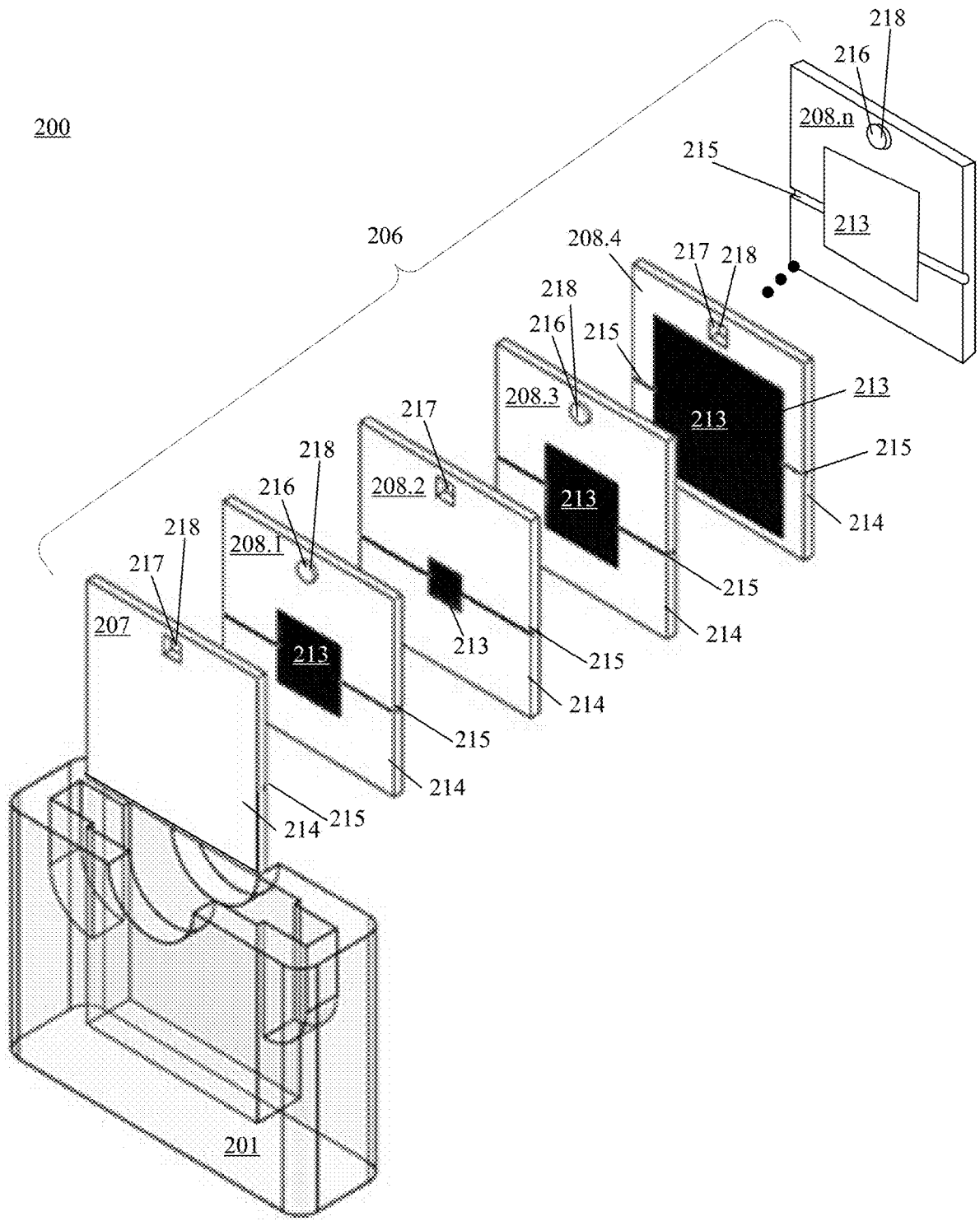
FIG. 2 shows an exploded view of a body cube.
Figure 3:
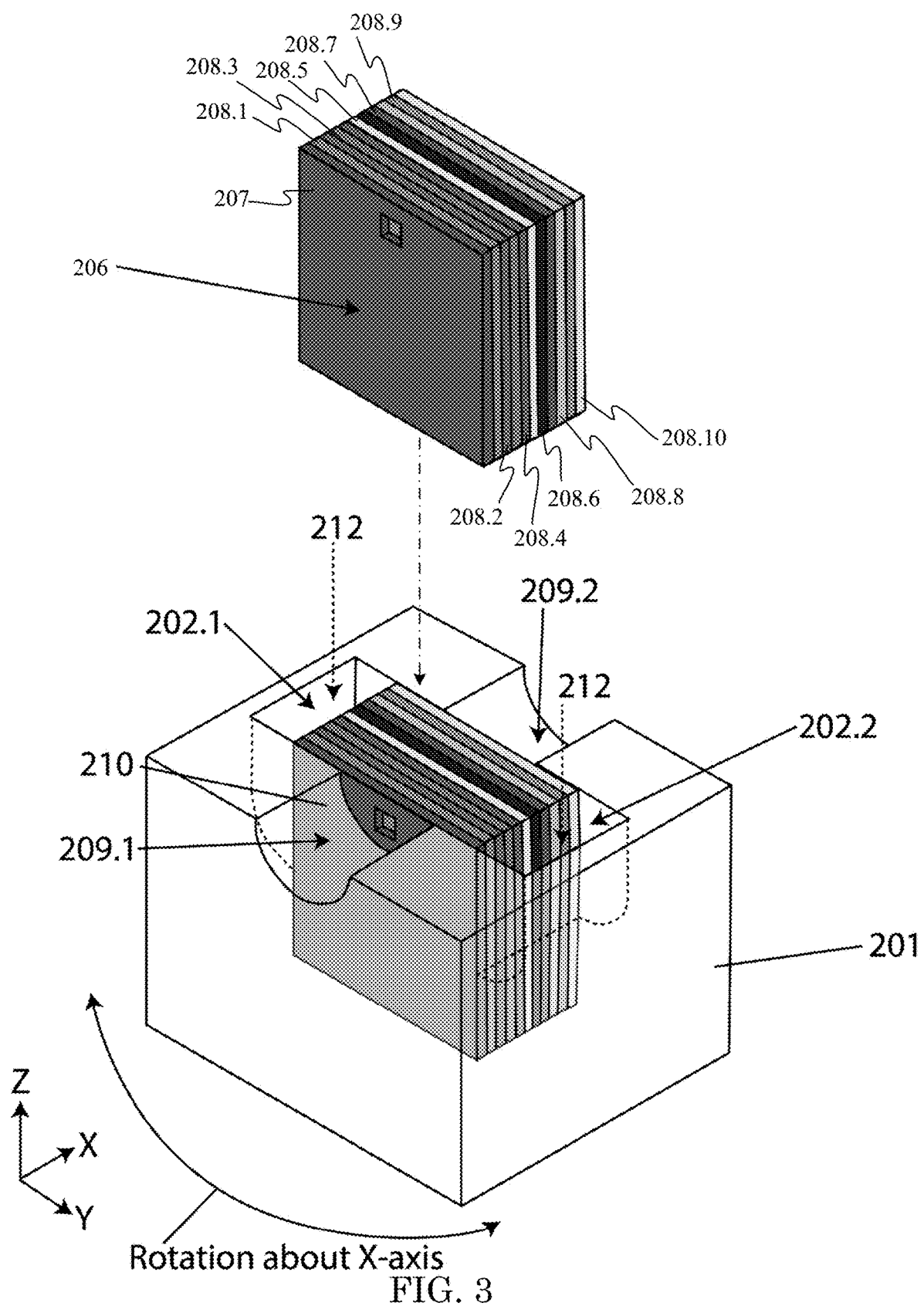
FIG. 3 shows insertion of body chips in an organ chip holder of a body cube.
Figure 4:
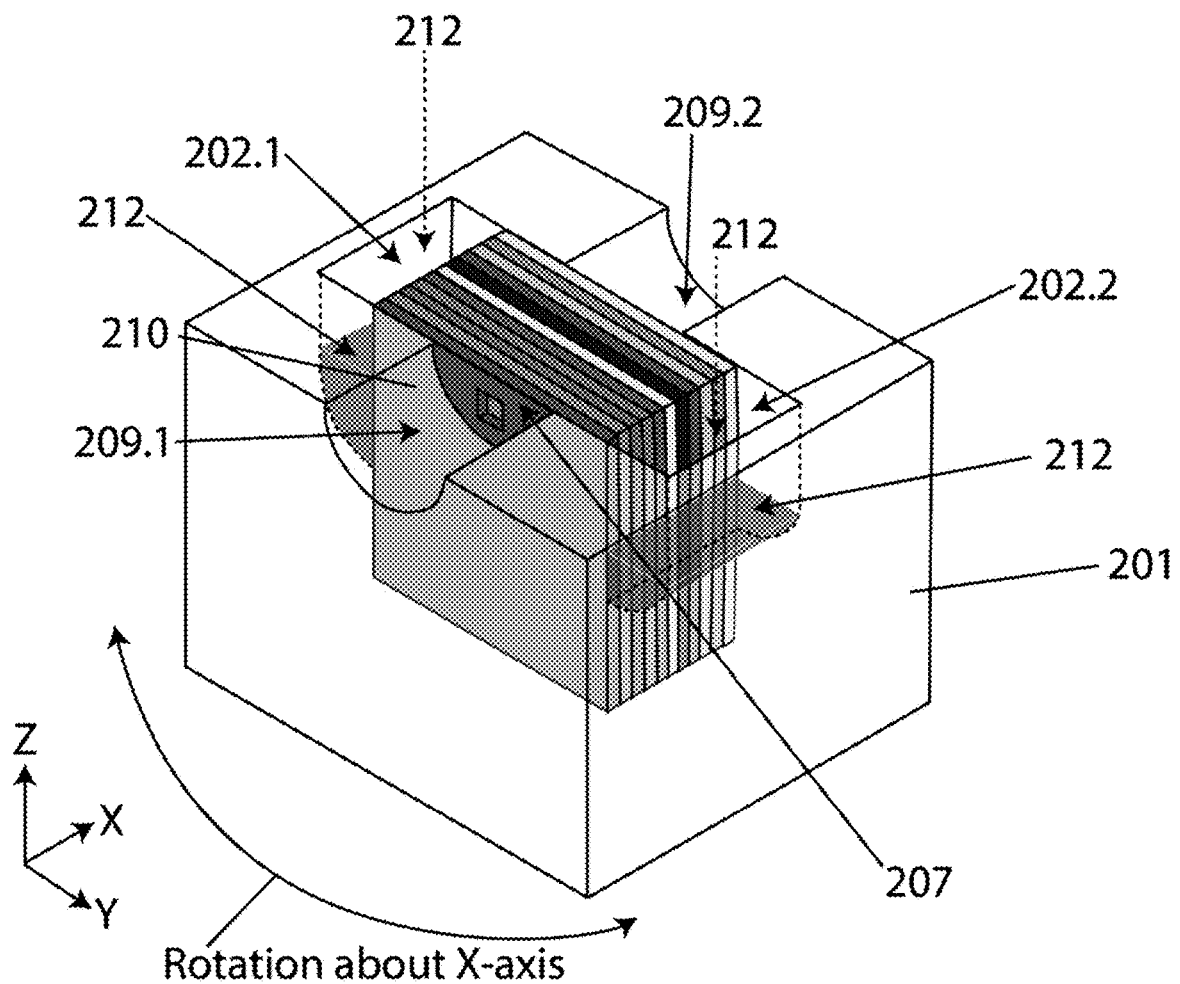
FIG. 4 shows a perspective view of a body cube with cell culture medium disposed in cell culture medium reservoirs.
Figure 5:
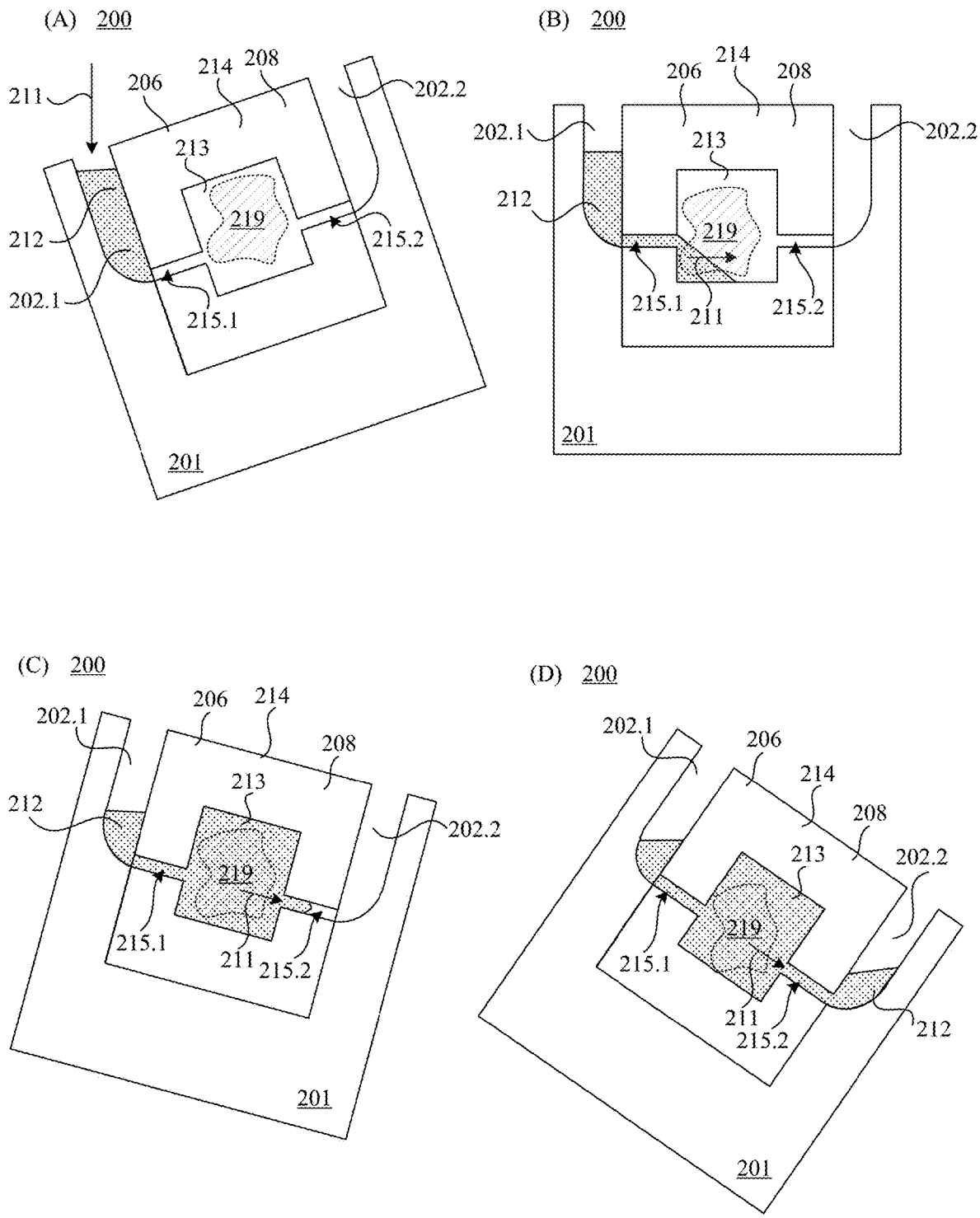
FIG. 5 shows communication of cell culture medium in various components of body cube in response to rotation of the body cube.
Figure 6:
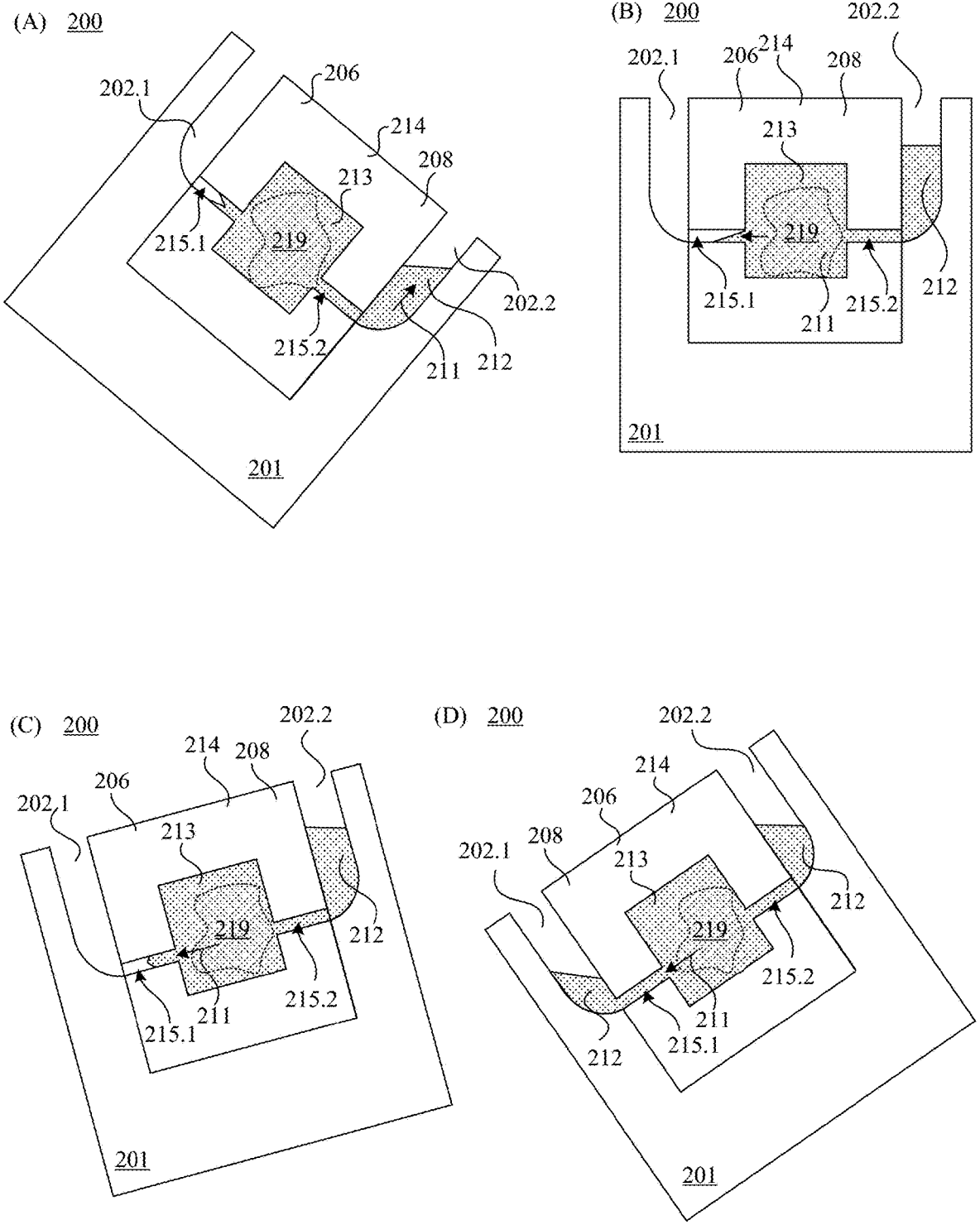
FIG. 6 shows communication of cell culture medium in various components of body cube in response to rotation of the body cube.
Figure 7:
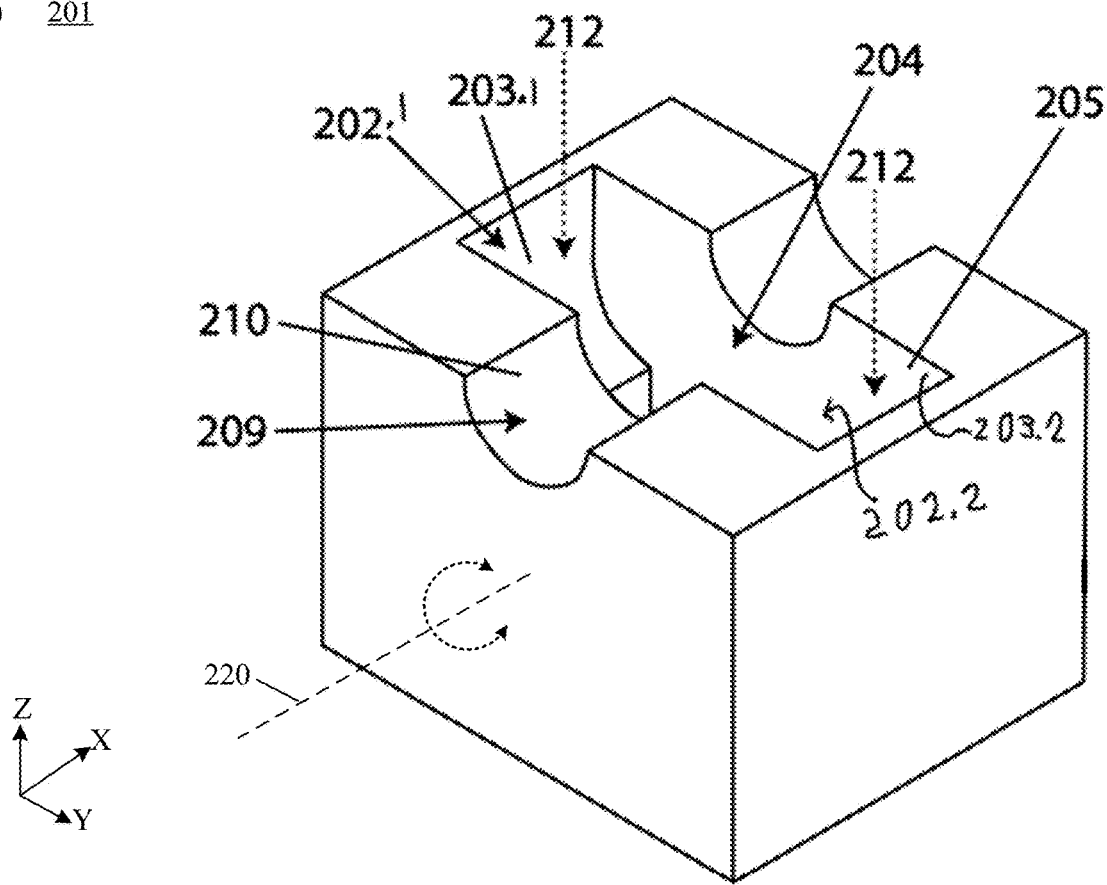
FIG. 7 shows a perspective view of an organ chip holder in panel A and plan view of the organ chip holder in panel B.
Figure 7:
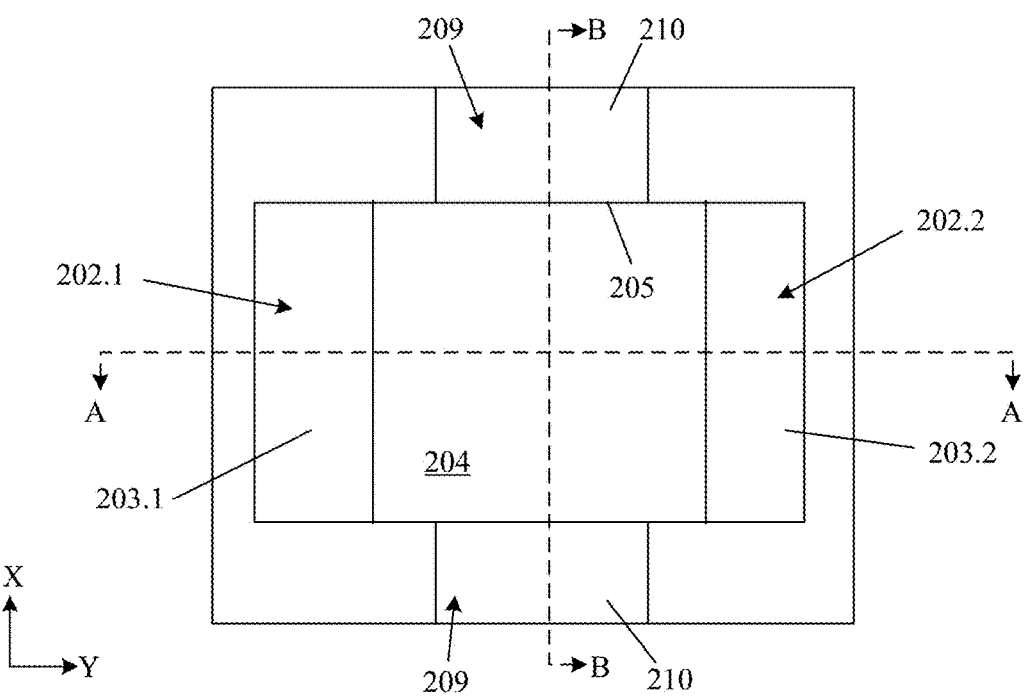
Figure 8:
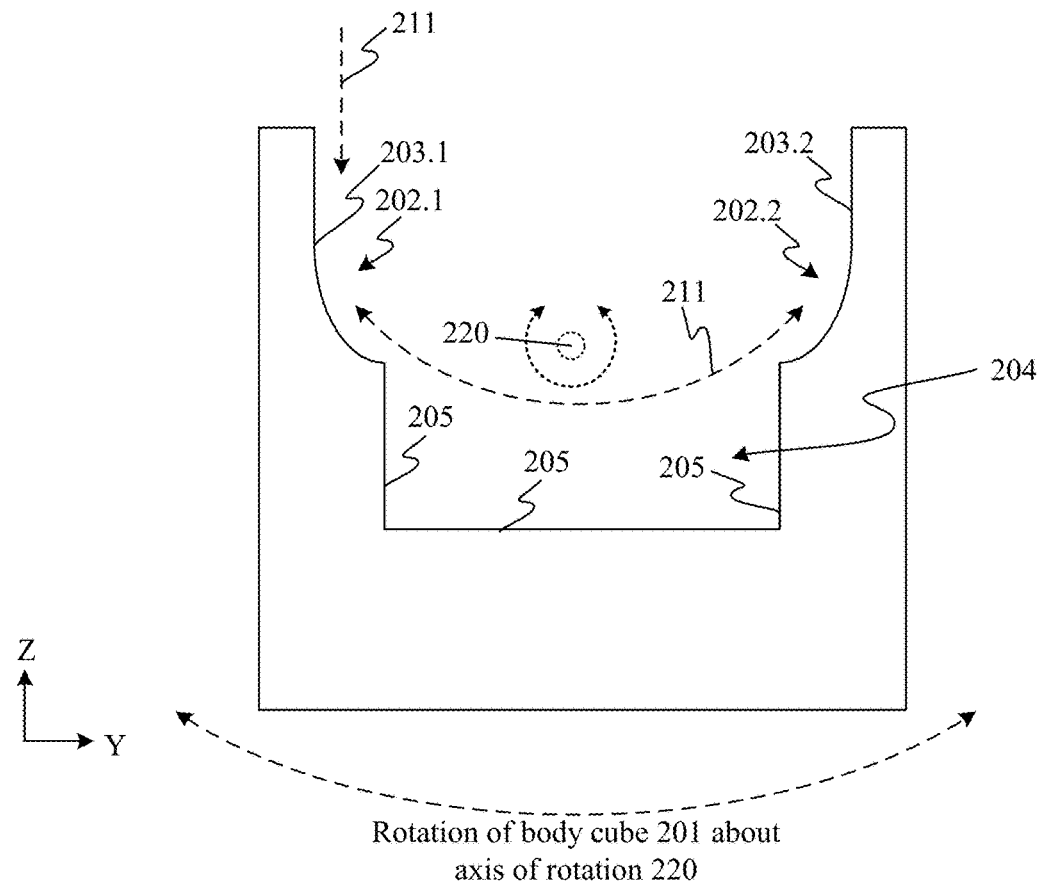
FIG. 8 shows a cross-section along line A-A (panel A) and along line B-B (panel B) of the organ chip holder shown in panel B of FIG. 7.
Figure 8:
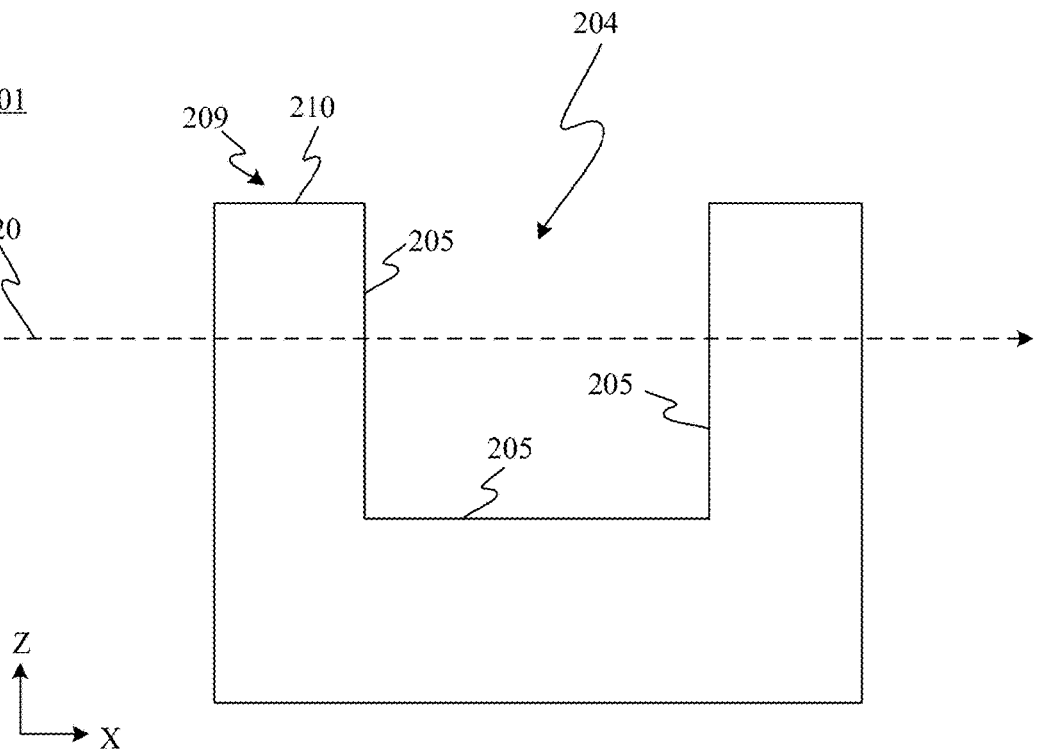
Figure 9:
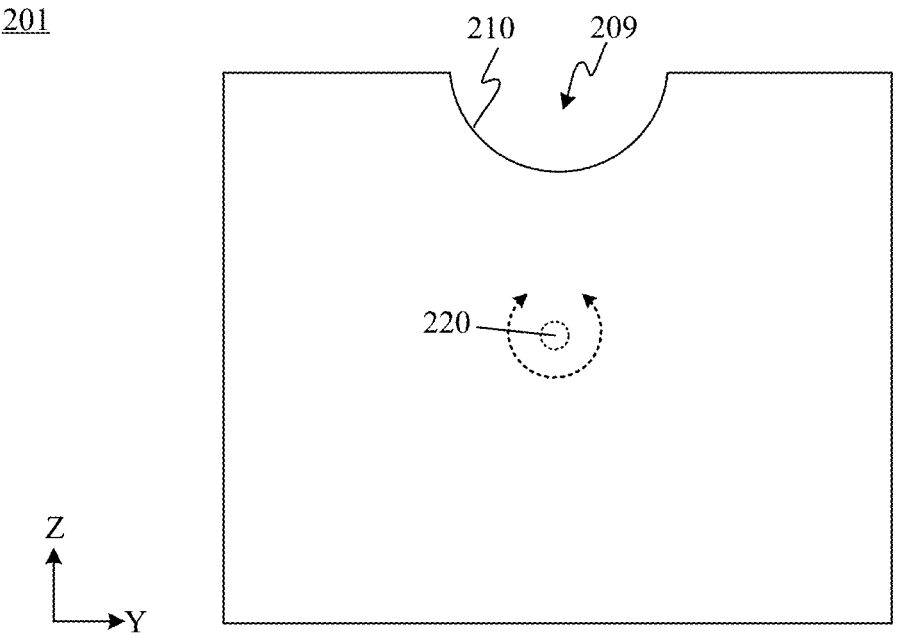
FIG. 9 shows side views in panel A and panel B of the body cube shown in FIG. 7.
Figure 9:
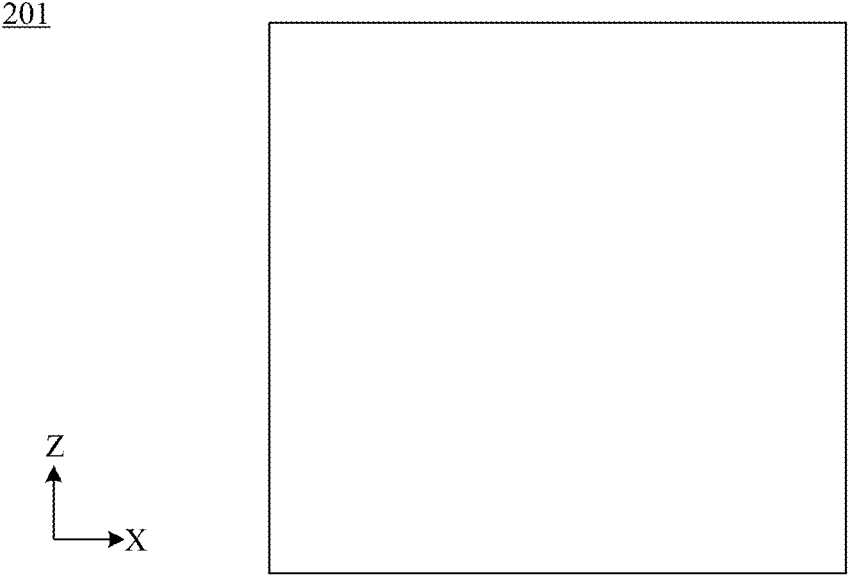

Body cube 200 cultures tissue. In an embodiment, with reference to FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, body cube 200 includes: organ chip holder 201; and body barrier chip 207 and first body organ chip 208.1 disposed in organ chip holder 201, first body organ chip 208.1 including first cell culture chamber 213.1 that receives cell culture medium 212 and produces first tissue 219.1 in first cell culture chamber 213.1, such that organ chip holder 201 receives cell culture medium 212 and communicates cell culture medium 212 to first cell culture chamber 213.1 of first body organ chip 208.1 in response to rotation of organ chip holder 201. Rotation, e.g., can occur about axis of rotation 220 as shown in FIG. 1 to provide communication of cell culture medium 212 as shown in FIG. 5 and FIG. 6.

In an embodiment, in the body cube 200, organ chip holder 201 includes first cell culture medium reservoir 202.1 that is bounded by first reservoir wall 203.1 and receives cell culture medium 212; and organ chip receiver 204 bounded by receiver wall 205 and that receives body barrier chip 207 and first body organ chip 208.1. Body barrier chip 207 is in mechanical engagement with receiver wall 205 so that body barrier chip 207 rotates with body cube 200. First body organ chip 208.1 is in mechanical engagement with receiver wall 205 and body barrier chip 207 so that body barrier chip 207, first body organ chip 208.1, and organ chip holder 201 rotate together in response to rotation of body cube 200. First body organ chip 208.1 further includes: body chip frame 214 that mechanically engages body organ chip 208 and receiver wall 205; first fluid medium communication channel 215.1 in fluid communication with first cell culture medium reservoir 202.1 and that: is disposed in body chip frame 214; and receives cell culture medium 212 from first cell culture medium reservoir 202.1, wherein first cell culture chamber 213.1 is bounded by body chip frame 214, is in fluid communication with first fluid medium communication channel 215.1, and receives cell culture medium 212 from first fluid medium communication channel 215.1 in response to rotation of body cube 200; and second fluid medium communication channel 215.2 in fluid communication with first cell culture chamber 213.1 and that: is disposed in body chip frame 214; and receives cell culture medium 212 from first cell culture chamber 213.1 in response to rotation of body cube 200.

In an embodiment, first body organ chip 208.1 further includes: primary tissue surface 223 on which is disposed first fluid medium communication channel 215.1, second fluid medium communication channel 215.2, and first cell culture chamber 213.1.

In an embodiment, first cell culture chamber 213.1 includes: chamber wall 226 that contacts cell culture medium 212; chamber protrusion 221 disposed on chamber wall 226 and that protrudes from chamber wall 226; and chamber flow channel 222 bounded by chamber wall 226 and chamber protrusion 221 and that receives cell culture medium 212 from first fluid medium communication channel 215.1 and communicates cell culture medium 212 to second fluid medium communication channel 215.2 and in which tissue 219 grows.

Figure 10:
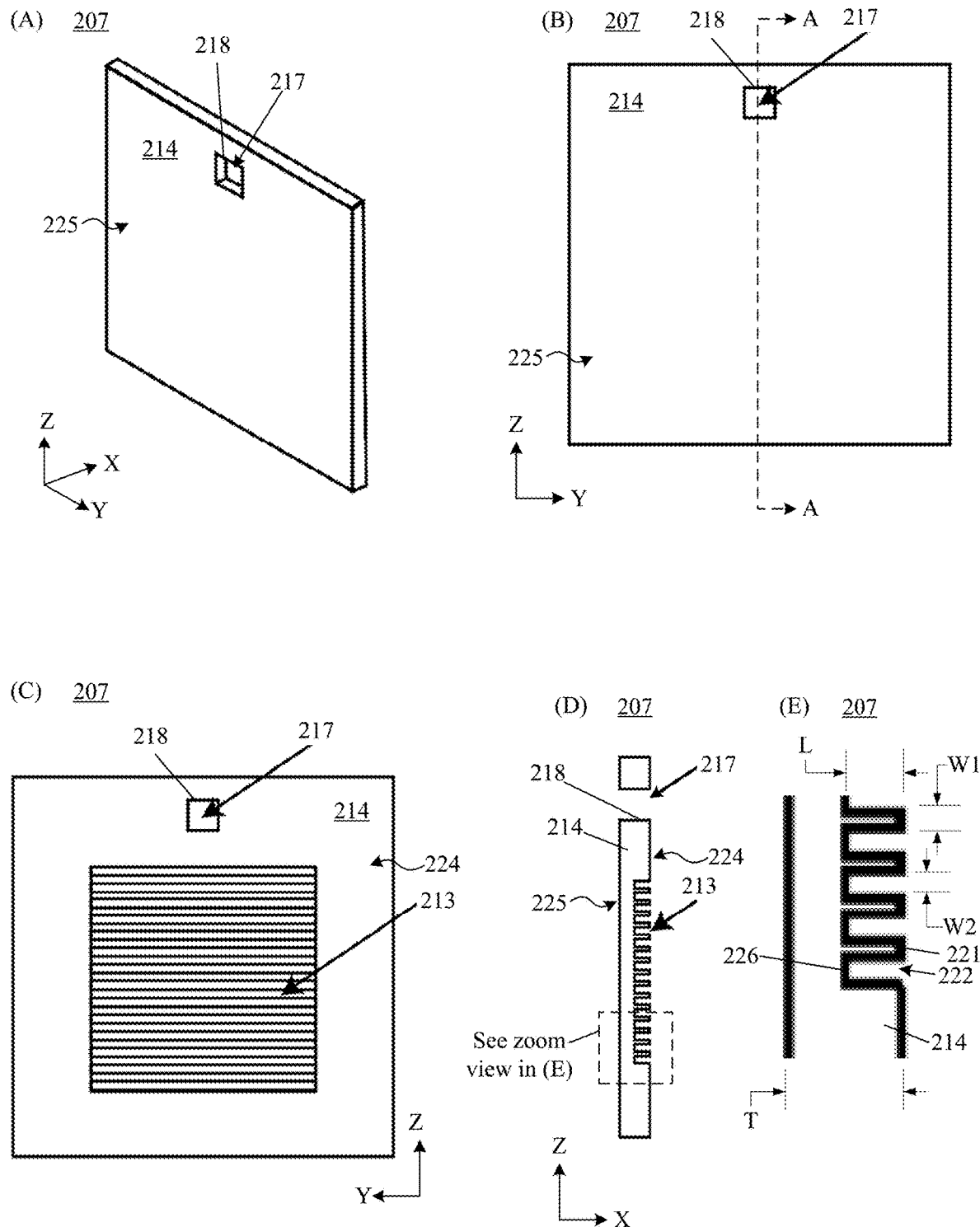
FIG. 10 shows for a body barrier chip: (A) a perspective view, (B) a barrier surface side, (C) a secondary tissue surface side, (D) a cross-section along line A-A from panel B, and (E) an enlarged portion of panel D.
Figure 11:
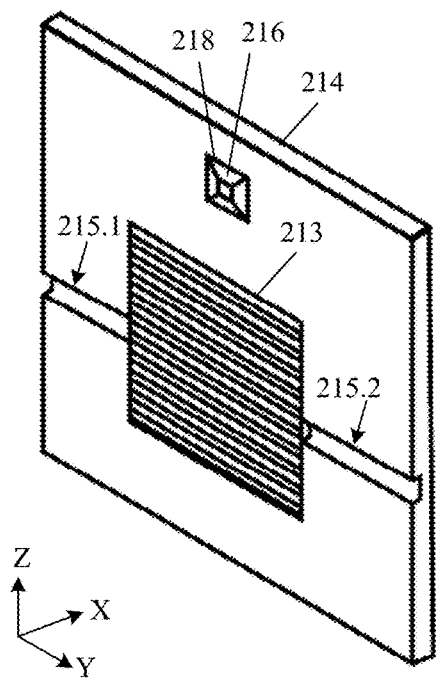
FIG. 11 shows for a body organ chip: (A) a perspective view, (B) a primary tissue surface side, and (C) a secondary tissue surface side.
Figure 11:
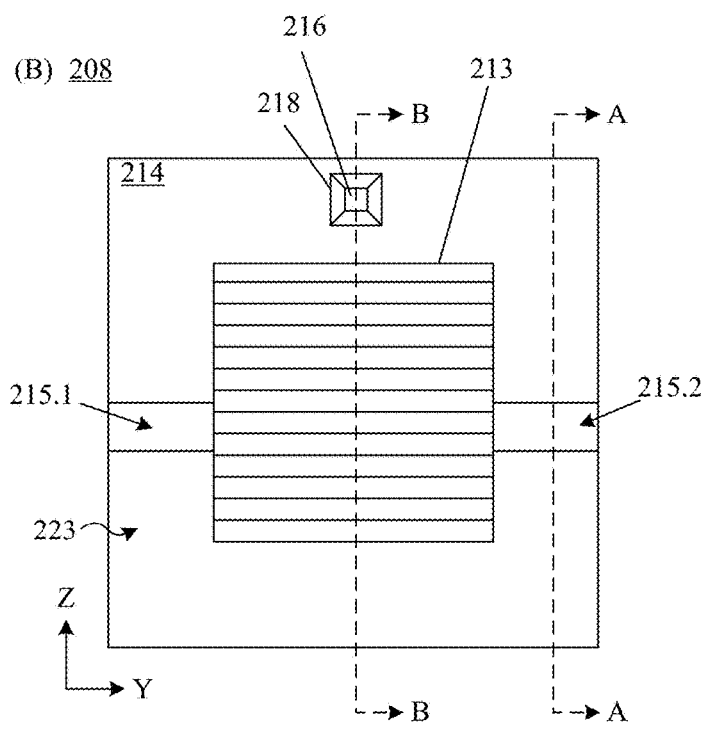
Figure 11:
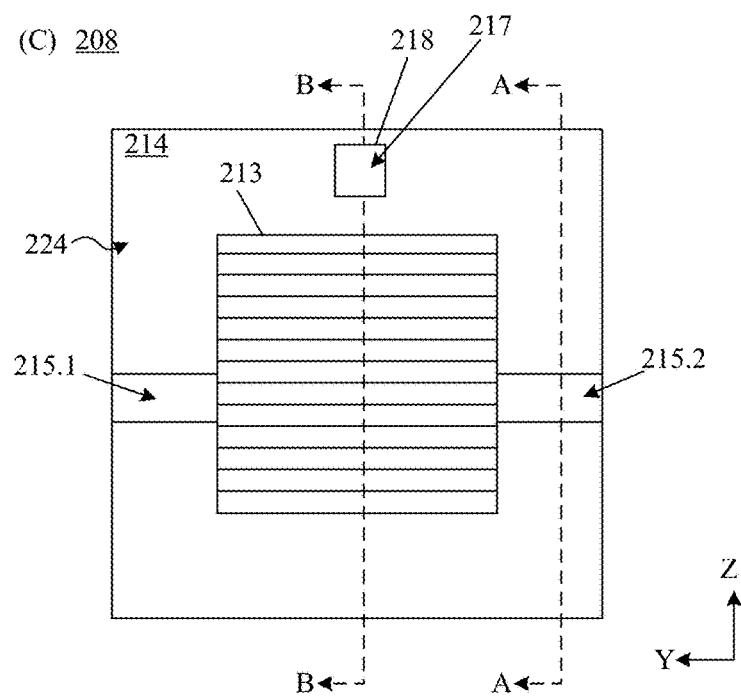
Figure 12:
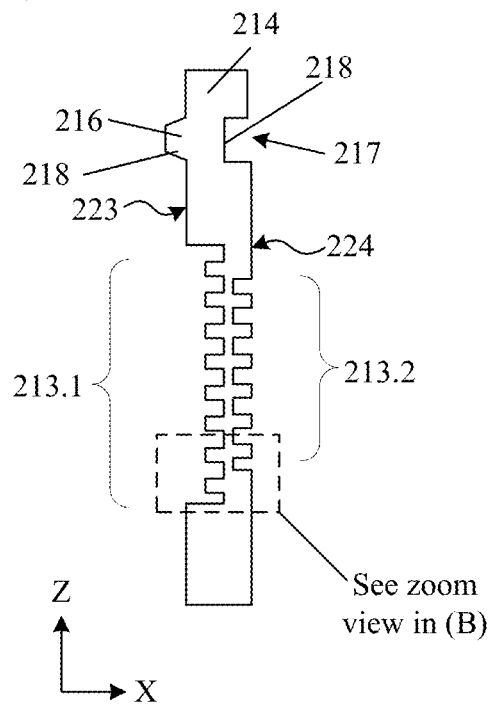
FIG. 12 shows for the body organ chip of FIG. 11: (A) a cross-section along line B-B from panel B of FIG. 11, (B) an enlarged portion of panel A, and (C)) a cross-section along line A-A from panel B of FIG. 11.
Figure 12:
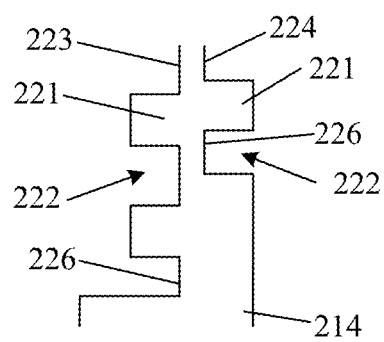
Figure 12:
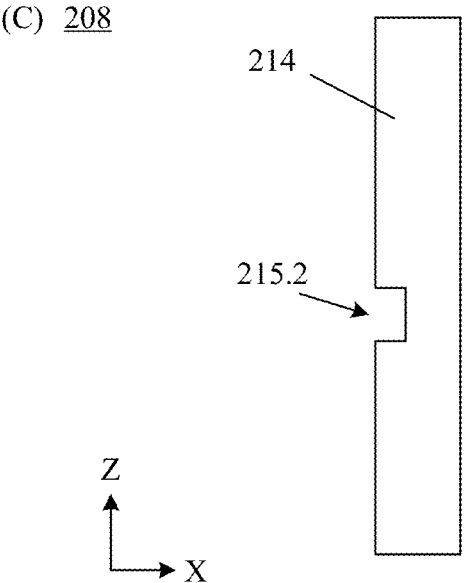
Figure 13:
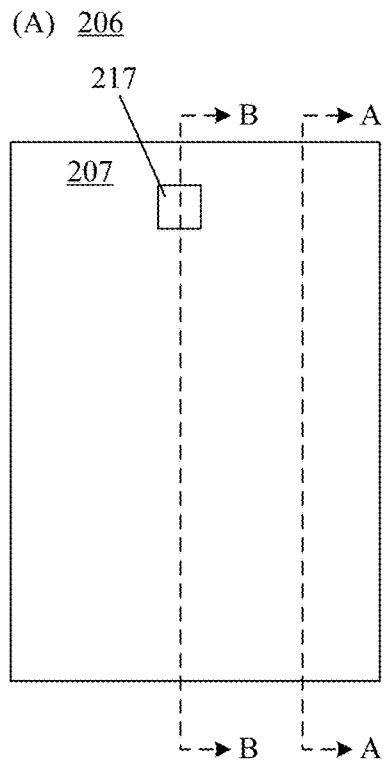
FIG. 13 shows for a stack of body chips: (A) a plan view, (B) a cross-section along a line B-B in panel A, and a cross-section along line A-A in panel A.
Figure 13:
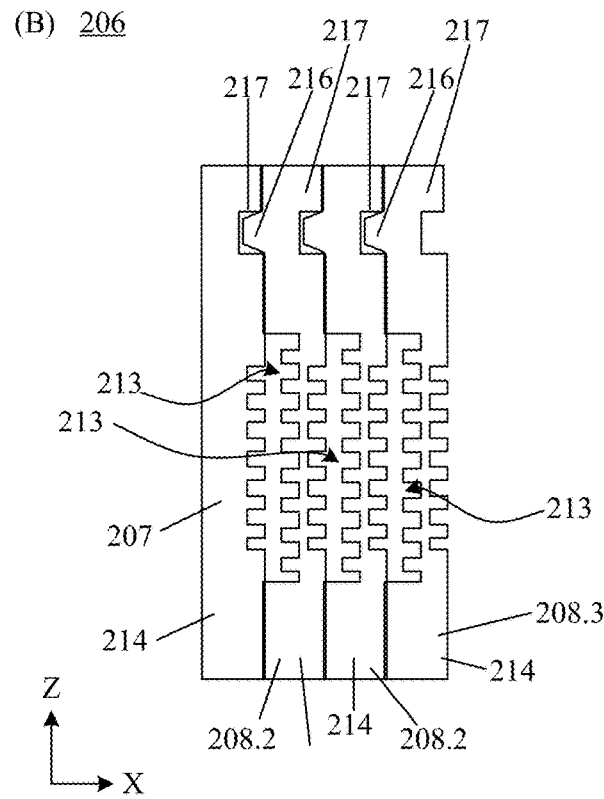
Figure 13:
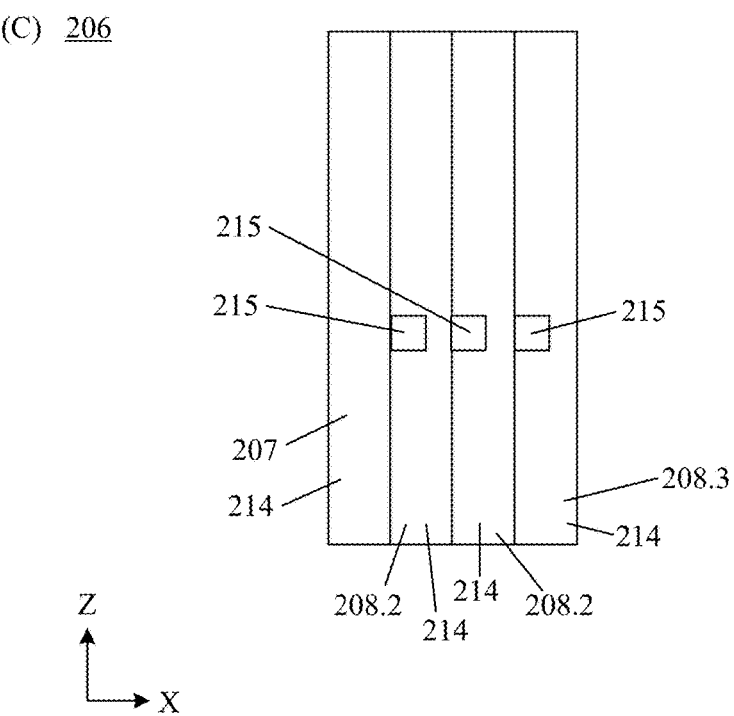

In an embodiment, body barrier chip 207 includes body chip frame 214 including: barrier surface 225 that mechanically engages receiver wall 205; and secondary tissue surface 224 opposite barrier surface 225 and that engages primary tissue surface 223 of first body organ chip 208.1; and alignment member 218 disposed on secondary tissue surface 224 of body chip frame 214 and that mechanically engages alignment member 218 on primary tissue surface 223 of first body organ chip 208.1. Although FIG. 10 shows body barrier chip 207 with cell culture chamber 213 disposed on secondary tissue surface 224, cell culture chamber 213 can be absent on body barrier chip 207 or secondary tissue surface 224 for functioning of body barrier chip 207 and functioning of body cube 200. Instead of including cell culture chamber 213, secondary tissue surface 224 can be a planar surface without culture chamber 213.

In an embodiment, body barrier chip 207 includes cell culture chamber 213 disposed on secondary tissue surface 224.

In an embodiment, cell culture chamber 213 of body barrier chip 207 includes: chamber wall 226 that contacts cell culture medium 212; chamber protrusion 221 disposed on chamber wall 226 and that protrudes from chamber wall 226; and chamber flow channel 222 bounded by chamber wall 226 and chamber protrusion 221 and that receives cell culture medium 212 from first fluid medium communication channel 215.1 of first body organ chip 208.1 and communicates cell culture medium 212 to second fluid medium communication channel 215.2 of first body organ chip 208.1 and in which first tissue 219.1 grows in cell culture chamber 213 of body barrier chip 207 and first cell culture chamber 213.1 of first body organ chip 208.1.

In an embodiment, first body organ chip 208.1 includes secondary tissue surface 224 opposite primary tissue surface 223 of first body organ chip 208.1; and second cell culture chamber 213.2 disposed on secondary tissue surface 224 of first body organ chip 208.1.

In an embodiment, second cell culture chamber 213.2 disposed on secondary tissue surface 224 of first body organ chip 208.1 includes: chamber wall 226; chamber protrusion 221 disposed on chamber wall 226 and that protrudes from chamber wall 226; and chamber flow channel 222 bounded by chamber wall 226 and chamber protrusion 221.

In an embodiment, first body organ chip 208.1 includes alignment member 218 disposed on secondary tissue surface 224.

In an embodiment, body cube 200 further includes second body organ chip 208.2 disposed in organ chip receiver 204 and in mechanical engagement with receiver wall 205 and first body organ chip 208.1, such that body barrier chip 207, first body organ chip 208.1, second body organ chip 208.2, and organ chip holder 201 rotate together in response to rotation of body cube 200, wherein first body organ chip 208.1 is interposed between body barrier chip 207 and second body organ chip 208.2.

In an embodiment, second body organ chip 208.2 includes first cell culture chamber 213.1 opposing second cell culture chamber 213.2 of first body organ chip 208.1, such that first cell culture chamber 213.1 of second body organ chip 208.2 and second cell culture chamber 213.1 of first body organ chip 208.1 in combination receive cell culture medium 212 and produce second tissue 219.2 in first cell culture chamber 213.1 of second body organ chip 208.2 and second cell culture chamber 213.2 of first body organ chip 208.1, and organ chip holder 201 communicates cell culture medium 212 to first cell culture chamber 213.1 of second body organ chip 208.2 and second cell culture chamber 213.2 of first body organ chip 208.1 in response to rotation of organ chip holder 201.

In an embodiment, second body organ chip 208.2 includes: body chip frame 214 that mechanically engages first body organ chip 208.1 and receiver wall 205; first fluid medium communication channel 215.1 in fluid communication with first cell culture medium reservoir 202.1 and that: is disposed in body chip frame 214; and receives cell culture medium 212 from first cell culture medium reservoir 202.1, wherein first cell culture chamber 213.1 of second body organ chip 208.2 is bounded by body chip frame 214 of second body organ chip 208.2, is in fluid communication with first fluid medium communication channel 215.1, and receives cell culture medium 212 from first cell culture medium reservoir 202.1 in response to rotation of body cube 200; and second fluid medium communication channel 215.2 in fluid communication with first cell culture chamber 213.1 of second body organ chip 208.2 and that: is disposed in body chip frame 214 of second body organ chip 208.2;

and receives cell culture medium 212 from first cell culture chamber 213.1 of second body organ chip 208.2 in response to rotation of body cube 200.

In an embodiment, second body organ chip 208.2 includes: primary tissue surface 223 on which is disposed first fluid medium communication channel 215.1, second fluid medium communication channel 215.2, and first cell culture chamber 213.1 of second body organ chip 208.2.

In an embodiment, first cell culture chamber 213.1 of the second body organ chip 208.2 includes: chamber wall 226 that contacts cell culture medium 212; chamber protrusion 221 disposed on chamber wall 226 and that protrudes from chamber wall 226; and chamber flow channel 222 bounded by chamber wall 226 and chamber protrusion 221 and that receives cell culture medium 212 from first fluid medium communication channel 215.1 of second body organ chip 208.2 and communicates cell culture medium 212 to second fluid medium communication channel 215.2 of second body organ chip 208.2 and in which second tissue 219.2 grows.

In an embodiment, body cube 200 includes organ chip holder 201 including: organ chip receiver 204 bounded by receiver wall 205 and that: receives a plurality of body chips 206 and cell culture medium 212; and communicates to body chips 206 a volume of cell culture medium 212 that is limited to a near-physiological amount or less of cell culture medium 212 for growing tissue 219; first cell culture medium reservoir 202.1 bounded by first reservoir wall 203.1 and in fluid communication with body chips 206 and that receives cell culture medium 212 and communicates cell culture medium 212 to body chips 206; second cell culture medium reservoir 202.2 bounded by second reservoir wall 203.2 and in fluid communication with body chips 206 and that receives cell culture medium 212 from body chips 206 in response to rotation of organ chip holder 201; body organ chips 206 disposed in organ chip receiver 204, such that that body organ chips 206 are mechanically engaged by receiver wall 205 so that body chips 206 rotate with organ chip holder 201 when organ chip holder 201 is subjected to rotation, and body chips 206 include: first body organ chip 208.1 including: first body chip frame 214; first fluid medium communication channel 215.1 disposed in first body chip frame 214.1 and in fluid communication with first cell culture medium reservoir 202.1, such that first fluid medium communication channel 215.1 receives cell culture medium 212 from first cell culture medium reservoir 202.1 and communicates cell culture medium 212 to first cell culture chamber 213.1; first cell culture chamber 213.1 disposed in first body chip frame 214.1 and in fluid communication with first fluid medium communication channel 215.1, such that first cell culture chamber 213.1: receives cell culture medium 212 from first fluid medium communication channel 215.1 in response to rotation of organ chip holder 201, such that a volume of cell culture medium 212 accommodated by first cell culture chamber 213.1 is limited to a near-physiological amount of cell culture medium 212; produces first tissue 219.1 disposed in first cell culture chamber 213.1; and provides contact between first tissue 219.1 and cell culture medium 212; and communicates cell culture medium 212 to second fluid medium communication channel 215.2; second fluid medium communication channel 215.2 disposed in first body chip frame 214.1 and in fluid communication with first cell culture chamber 213.1 and that receives cell culture medium 212 from first cell culture chamber 213.1 in response to rotation of organ chip holder 201; body barrier chip 207 in mechanical engagement with receiver wall 205 and first body organ chip 208.1 by alignment member 218, body barrier chip 207 including: body chip frame 214; alignment member 218 disposed in body chip frame 214 to mechanically engage first body organ chip 208.1; and cell culture chamber 213 bounded by body chip frame 214 and opposing first cell culture chamber 213.1 of first cell culture chamber 213.1, wherein first tissue 219.1 grows between cell culture chamber 213 of body barrier chip 207 and first cell culture chamber 213.1 of first body organ chip 208.1.

As used herein, physiological amount refers to an amount (e.g., a volume, concentration, and the like) of a material that is present under normal biological conditions in volume of tissues that is due neither to anything pathologic nor significant in terms of causing illness and includes near-physiological amount that does not cause illness and that occurs at an average level found in healthy individuals. In contrast, supraphysiologic amount is an amount that is elevated compared to an average level found in healthy individuals to an extent that disrupts normal, healthy physiology. Accordingly, a near-physiological amount of cell culture medium 212 can be slightly greater than or slightly less than a physiological amount, depending on a particular tissue or organ subjected to cell culture medium 212. In an embodiment, a near-physiological amount of cell culture medium 212 includes a volumetric amount of cell culture medium 212 relative to the physiological amount is from 0% to ±20%, specifically from 0% to ±1%, and more specifically from 0% to ±0.1% of the physiological amount. In an embodiment, a near-physiological amount of cell culture medium 212 is from 1 microliter (μL) to 100 milliliters (mL), specifically from 1 μL to 10 mL, and more specifically from 1 μL to 100 μL.

Organ chip holder 201 includes organ chip receiver 204 sized to allow body chips 206 to be removably inserted therein. Beyond body organ chip 208 and first body organ chip 208.1, organ chip receiver 204 can be sized to receive any number of body organ chip 208 in combination. Although organ chip holder 201 is shown as having single organ chip receiver 204, organ chip holder 201 can include any number of organ chip receivers 204 located therein to receive and house body chips 206. A shape and size of organ chip receiver 204 is contemplated to receive an arbitrary number or shape of body chips 206. Body chips 206 are received in organ chip receiver 204 so that cell culture medium 212 is communicated to cell culture chamber 213 of body chip 206 in absence of pooling cell culture medium 212 in organ chip receiver 204 to an exclusion of communication to body chip 206. As shown in FIG. 5, FIG. 6, FIG. 7, and FIG. 8, when organ chip holder 201 is subjected to rotation about axis of rotation 220 that can be, e.g., orthogonal to barrier surface 225 of body barrier chip 207, cell culture medium 212 is communicated between cell culture medium reservoirs 202 and cell culture chambers 213. In some embodiment, a pump produces fluidic flow so that cell culture medium 212 is communicated between cell culture medium reservoirs 202 and cell culture chambers 213.

First cell culture medium reservoir 202.1 and second cell culture medium reservoir 202.2 independently have an arbitrary shape and volume respectively bounded by first reservoir wall 203.1 and second reservoir wall 203.1 to accommodate cell culture medium 212 in an amount that provides a near-physiological amount of cell culture medium 212 to each cell culture chamber 213 of body chips 206. Accordingly, reservoir wall 203 or receiver wall 205 do not block fluid communication of cell culture medium 212 between cell culture medium reservoir 202 and fluid medium communication channel 215. A volume of cell culture medium reservoir 202 can be from 1 μL to 1 liter (L), specifically from 1 µL to 100 mL, and more specifically from 1 µL to 1 mL. Although reservoir wall 203 is shown as being concave with respect to body chip 206 disposed in organ chip receiver 204, reservoir wall 203 can have an arbitrary shape selected to communicate cell culture medium 212 with fluid medium communication channels 215 of body organ chips 208.

Organ chip receiver 204 provided by receiver wall 205 is shown as having a cuboidal or parallelepiped shape but can have any other shapes such as spherical or ellipsoidal, by way of example only. Further, organ chip receiver 204 accommodates disposition of an arbitrary number of body chips 206.

Organ chip holder 201 optionally can include body chip access indentation 209 bounded by body chip access indentation wall 210. Body chip access indentation 209 provides an access to an interior of organ chip holder 201 for disposing body chip 206 in organ chip receiver 204 or removal of body chip 206 from organ chip receiver 204. Body chip access indentation 209 can be large enough to accommodate a removal device, e.g., forceps, tweezers, and the like or fingers or robotic digits.

Body chips 206 include body barrier chip 207 and body organ chip 208. Body chip 206 is configured to be removably inserted into organ chip receiver 204 and can have a thickness T from 0.05 millimeter (mm) to 1 centimeters (cm), specifically from 0.05 mm to 0.5 cm, and more specifically from 0.05 mm to 0.25 cm. Moreover, the size of body chips 206 is selected so that the fit in organ chip receiver 204 is snug but can be press-fit while remaining removeable from organ chip receiver 204, wherein body chips 206 contact organ chip receiver 204 through body chip frame 214 so that as organ chip holder 201 moves, e.g., through rotation or translation, body chips 206 move.

Body barrier chip 207 provides a barrier for fluid communication from all cell culture chambers 213 to organ chip receiver 204 and prevents cell culture medium 212 from being communicated from body chips 206 to organ chip receiver 204. In this manner, cell culture medium 212 essentially flows between cell culture medium reservoirs 202 and cell culture chambers 213 in an absence of communication with organ chip receiver 204. Moreover, body chip frame 214 of body chips 206 also prevent fluid flow of cell culture medium 212 from cell culture chamber 213 to organ chip receiver 204 so that even though body chips 206 are individual components that are combined in a stack in organ chip receiver 204, cell culture medium 212 does not leak from opposing cell culture chamber 213 of adjacent body chips 206.

Body barrier chip 207 includes barrier surface 225 on an opposing side with respect to secondary tissue surface 224. Barrier surface 225 prevents flow of cell culture medium 212 from body chip 206 to organ chip receiver 204 and contacts receiver wall 205 of organ chip holder 201. Alignment member 218 is disposed in body chip frame 214 for interlocking body barrier chip 207 to body organ chip 208. Alignment member 218 can be alignment receiver 217 or alignment protrusion 216, wherein alignment receiver 217 is an indentation in body chip frame 214 to receive alignment protrusion 216 that protrudes from an adjacent body chip 206. In this manner adjacent body chips 206 are mechanically engaged so that the stack of body chips 206 disposed in organ chip receiver 204 remain as a monolithic stack that are aligned and move together without leaking cell culture medium 212 from cell culture chamber 213 to organ chip receiver 204.

Body barrier chip 207 can include cell culture chamber 213 disposed on secondary tissue surface 224 and bounded by body chip frame 214. Cell culture chamber 213 includes a plurality of chamber protrusion 221 disposed on chamber wall 226 and that bound chamber protrusion 221 arranged between adjacent chamber protrusion 221. Although chamber protrusion 221 is shown as a straight axial structure that runs a length of cell culture chamber 213, chamber protrusion 221 can be various other shapes including, posts of various shapes, and curved or segmented shapes that can include serpentine and other shapes. Chamber flow channel 222 provides an enclave for growth and receipt of tissue and organ formation. Chamber protrusion 221 in combination with chamber flow channel 222 provide for structural support, mechanical strength, and directional flow of cell culture medium 212 in cell culture chamber 213. A width W1 of chamber protrusion 221 can be from 1 micrometer (µm) to 10 centimeters (cm), specifically from 1 micrometer (µm) to 1 cm. A width W2 of chamber flow channel 222 can be from 1 micrometer (µm) to 10 centimeters (cm), specifically from 1 micrometer (µm) to 1 cm. A length L of chamber protrusion 221 can be from 1 micrometer (µm) to 10 centimeters (cm), specifically from 1 micrometer (µm) to 1 cm.

Figure 14:
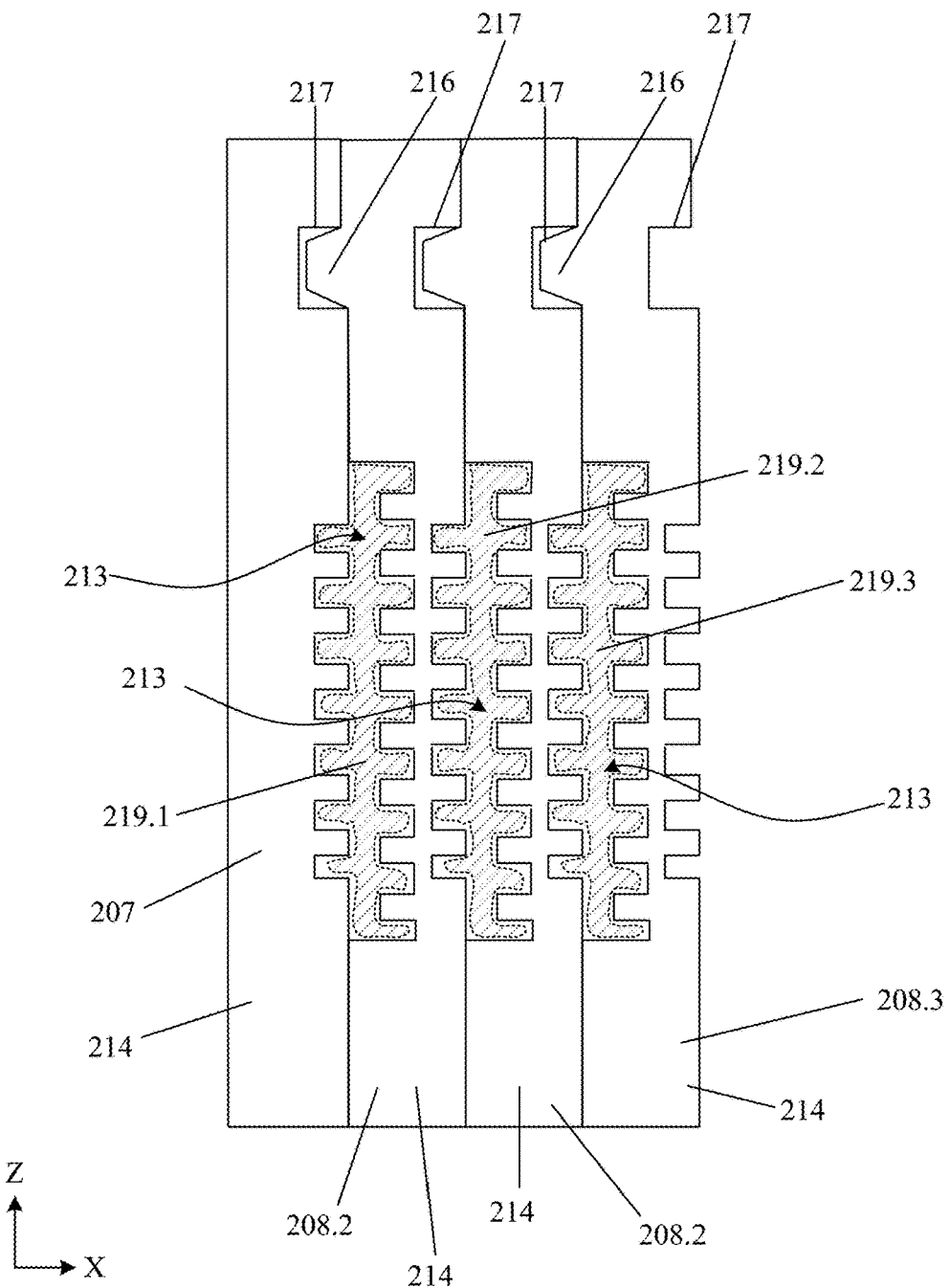
FIG. 14 shows an enlarged view of the cross-section of the stack of chips shown in FIG. 13 with tissues disposed in cell culture chambers.

Body organ chip 208 includes first cell culture chamber 213.1 and may include second cell culture chamber 213.2 disposed on opposing surfaces respectively, primary tissue surface 223 and secondary tissue surface 224. Each cell culture chamber 213 is bounded by body chip frame 214. Cell culture chamber 213 includes a plurality of chamber protrusion 221 disposed on chamber wall 226 and that bound chamber protrusion 221 arranged between adjacent chamber protrusion 221. Although chamber protrusion 221 is shown as a straight axial structure that runs a length of cell culture chamber 213, chamber protrusion 221 can be various other shapes including, posts of various shapes, and curved or segmented shapes that can include serpentine and other shapes. Chamber flow channel 222 provides an enclave for growth and receipt of tissue and organ formation. Chamber protrusion 221 in combination with chamber flow channel 222 provide for structural support, mechanical strength, and directional flow of cell culture medium 212 in cell culture chamber 213. A width W1 of chamber protrusion 221 can be from 1 micrometer (µm) to 10 centimeters (cm), specifically from 1 micrometer (µm) to 1 cm. A width W2 of chamber flow channel 222 can be from 1 micrometer (µm) to 10 centimeters (cm), specifically from 1 micrometer (µm) to 1 cm. A length L of chamber protrusion 221 can be from 1 micrometer (µm) to 10 centimeters (cm), specifically from 1 micrometer (µm) to 1 cm. It should be appreciated that first cell culture chamber 213.1 and second cell culture chamber 213.2 are independent, and any component of first cell culture chamber 213.1 can have a same or different size, shape, or structural configuration than second cell culture chamber 213.2. In an embodiment, chamber protrusions 221 disposed in first cell culture chamber 213.1 have length L that is different (e.g., shorter) than the length of chamber protrusions 221 disposed in second cell culture chamber 213.2 so that when body chip 206 are stacked, tissue 219 can form in the two opposing cell culture chambers 213, e.g., as shown in FIG. 14 for first tissue 219.1, second tissue 219.2, and third tissue 219.3. In an embodiment, body organ chip 208 does not include second cell culture chamber 213.2 disposed on opposing surfaces respectively, primary tissue surface 223 and secondary tissue surface 224.

Body organ chip 208 includes first fluid medium communication channel 215.1 and second fluid medium communication channel 215.2 that are respectively in fluid communication with first cell culture medium reservoir 202.1 and second cell culture medium reservoir 202.2 of organ chip holder 201. Moreover, fluid medium communication channels 215 are disposed on primary tissue surface 223 and seal against secondary tissue surface 224 of an adjacent body chip 206 when body chips 206 are stacked as shown, e.g., in FIG. 1., FIG. 13, and FIG. 14. First cell culture medium reservoir 202.1 and second cell culture medium reservoir 202.2 are sized as to provide cell culture medium 212 to and from cell culture chamber 213. In this respect, a cross-sectional size of fluid medium communication channel 215 perpendicular to flow of cell culture medium 212 in fluid medium communication channel 215 can be from 1 µm² to 10 cm², specifically 1 µm² to 1 cm², and more specifically from 1 µm² to 10 mm². A length of fluid medium communication channel 215 from organ chip receiver 204 to cell culture chamber 213 can be from 1 µm to 100 cm, specifically 1 µm to 1 cm, and more specifically from 1 µm to 50 mm. Moreover, first fluid medium communication channel 215.1 and second fluid medium communication channel 215.2 have dimensions configured to provide a selected flow rate of cell culture medium 212 delivered to cell culture chamber 213. The flow rate can be selectively tailorable and can be substantially similar to a physiological flow rate in a section of an organ similar in size to the tissue cultured in cell culture chamber 213, such as a section of liver or GI tract.

With reference to FIG. 1, FIG. 2, FIG. 13, and FIG. 14, body chip 206 are stacked and disposed in organ chip receiver 204, wherein tissue 219 forms in two opposing cell culture chambers 213, or in one cell culture chamber 213 and the secondary tissue surface 224 of body chips 206. That is, opposing cell culture chamber 213 of adjacent body chips 206 house a cellular tissue, such as liver tissue, kidney tissue, gastrointestinal tract tissue, lung tissue, skin tissue, brain tissue, or heart tissue, by way of example. It is contemplated that cell culture chamber 213 can include a porous membrane or 3D scaffold disposed in cell culture chamber 213 to seed cellular tissue. A number of body barrier chips 207 and of body chips 206 can be selected based on a number of tissues 219 to be formed. The particular tissue formed in each pair of opposing cell culture chamber 213 can be the same or different. In this manner, body cube 200 can grow a select organ, set of organs, or an organ system that can include liver tissue, kidney tissue, gastrointestinal tract tissue, lung tissue, skin tissue, brain tissue, heart tissue, or any other tissue present in the human body, a combination thereof, or artificially created tissues that do not exist inside the human body. Similarly, body cube 200 can grow a select organ, set of organs, or an organ system that can include liver tissue, kidney tissue, gastrointestinal tract tissue, lung tissue, skin tissue, brain tissue, heart tissue, or any other tissue present in the body of any animal, a combination thereof, or artificially created tissues that do not exist inside the animal body. Volume ratios of tissues grown within body cube 200 can replicate organ volume ratios found in the human or animal body. Alternatively, tissues grown within body cube 200 do not need to replicate organ volume ratios found in the human or animal body. The modularity of body chips 206 allow different tissues having different growth periods to be developed separately and then used with body cube 200.

According to an embodiment, cell culture medium 212 is a blood surrogate that can include hemoglobin-based oxygen carriers, such as stroma-free hemoglobin, chemically cross-linked hemoglobin, polymerized hemoglobin, polymer conjugated hemoglobin, encapsulated hemoglobin, and perfluorocarbon-based oxygen carriers, such as perfluoroalkyl ethers, perfluoro crown ethers such as perfluoro-15-crown-5-ether, perfluoroalkanes such as perfluoropentane, perfluorohexane, perfluorononane, perfluorohexyl bromide, perfluorooctyl bromide, and perfluorodecyl bromide, perfluoroalkenes such as bisperfluorobutylethylene, perfluorocycloalkanes such as perfluorodecalin, perfluorocyclohexanes, perfluoroadamantane, perfluorobicyclodecane, and perfluoromethyl decahydroquinoline, perfluoro amines such as perfluoroalkyl amines, and C1-C8 substituted compounds thereof, isomers thereof, and combinations thereof. In an embodiment, cell culture medium 212 includes a drug having a selected concentration.

Body cube 200 can be made in various ways. It should be appreciated that body cube 200 includes a number of components, wherein such components can be interconnected and placed in communication by physical or chemical interconnects. Elements of body cube 200 can be formed from polydimethylsiloxane, plastic (including a thermoplastic), or silicon although other suitable materials, such ceramic, glass, or metal can be used. According to an embodiment, the elements of body cube 200 are formed using 3D printing although the elements of body cube 200 can be formed using other methods, such as injection molding or machining a stock material such as block of material that is subjected to removal of material such as by cutting, laser ablation, and the like. Accordingly, body cube 200 can be made by additive or subtractive manufacturing. In an embodiment, elements of body cube 200 are 3D printed to culture tissue that can include organs (e.g., liver, GI tract, kidney, and bone marrow) in body cube 200 using a physiological liquid volume.

Body cube 200 has numerous advantageous and unexpected benefits and uses. In an embodiment, with reference to FIG. 4, FIG. 5, and FIG. 6, a process for culturing tissue with body cube 200 includes: receiving cell culture medium 212 in first cell culture medium reservoir 202.1 of body cube 200; rotating cell culture medium reservoir 202; communicating cell culture medium 212 from first cell culture medium reservoir 202.1 to first fluid medium communication channel 215.1 of body organ chip 208 in response to rotating body cube 200, body organ chip 208 disposed in organ chip receiver 204 of organ chip holder 201 of body cube 200; receiving, by first fluid medium communication channel 215.1, cell culture medium 212 from first cell culture medium reservoir 202.1; communicating cell culture medium 212 from first fluid medium communication channel 215.1 to cell culture chamber 213 of the body organ chip 208 in response to rotating body cube 200; receiving, by first cell culture chamber 213.1, cell culture medium 212 from first fluid medium communication channel 215.1; and growing tissue 219 in cell culture chamber 213 in response to receiving cell culture medium 212 in cell culture chamber 213 to culture tissue.

According to an embodiment, the process for culturing tissue further includes: communicating cell culture medium 212 from cell culture chamber 213 to second fluid medium communication channel 215.2 of body organ chip 208 in response to rotating body cube 200; and receiving, by second fluid medium communication channel 215.2, cell culture medium 212 from cell culture chamber 213.

According to an embodiment, the process for culturing tissue further includes: communicating cell culture medium 212 from first cell culture medium reservoir 202.1 to second body organ chip 208 in response to rotating body cube 200, second body organ chip 208 disposed in organ chip receiver 204 of organ chip holder 201 of body cube 200 and in mechanical engagement with body organ chip 208; receiving, by cell culture chamber 213 of second body organ chip 208.2, cell culture medium 212 from first cell culture medium reservoir 202.1; and growing second tissue 219.2 in cell culture chamber 213 of second body organ chip 208.2 in response to receiving cell culture medium 212 in cell culture chamber 213 of second body organ chip 208.2.

Cell culture medium 212 can be communicated to cell culture chamber 213 through fluid medium communication channel 215 by alternately rotating organ chip holder 201 between a clockwise rotation about axis of rotation 220 (FIG. 5, wherein panels A to D show sequential clockwise rotation of organ chip holder 201) to a counter-clockwise rotation (FIG. 6, wherein panels A to D show sequential counter-clockwise rotation of organ chip holder 201). Alternately rotation of body cube 200 allows cell culture medium 212 to flow by gravity. Cell culture medium reservoir 202 can be rotated from +90° to −90° degrees about axis of rotation 220. Body cube 200 can be rotated by hand or by a machine. In some embodiments, a pump supplies cell culture medium 212 to cell culture medium reservoir 202. The pump can be an externally connected pump, or an integrated microfabricated pump. The pump can create unidirectional or bidirectional flow inside body cube 200. In some embodiments, body cube 200 includes a flow-rectifying structure that provides unidirectional flow, wherein cell culture medium 212, e.g., blood surrogate, from cell culture medium reservoir 202.2 flows directly to cell culture medium reservoir 202.1 without flowing through cell culture chamber 213. Once the blood surrogate is relocated to cell culture medium reservoir 202.1, it again flows through cell culture chamber 213 to reach cell culture medium reservoir 202.2.

In an embodiment, a process for delivering cell culture medium 212 to tissue 219 includes seeding a first cellular tissue in first cell culture chamber 213.1 of first body organ chip 208.1; disposed first body organ chip 208.1 in organ chip receiver 204 of organ chip holder 201. Cell culture medium 212 is provided in first cell culture medium reservoir 202.1 or second cell culture medium reservoir 202.2 of organ chip holder 201. Fluid medium communication channels 215 and cell culture medium reservoirs 202 are positioned in fluid communication. Cell culture medium 212 is delivered to cell culture chambers through first fluid medium communication channel 215.1 or second cell culture medium reservoir 202.2 by alternately rotating body cube 200 clockwise and counter-clockwise with respect to axis of rotation 220.

In an embodiment, a process for simulating human metabolism in body cube 200 includes providing a stacked set of body chip 206 that have been prepared by: seeding a GI tract tissue in first cell culture chamber 213.1 of first body organ chip 208.1 and cell culture chamber 213 of body organ chip 208; and seeding liver tissue in second cell culture chamber 213.2 of first body organ chip 208.1 and first cell culture chamber 213.1 of second body organ chip 208.2. The stack of body chip 206 including the seeded GI tract tissue and the seeded liver tissue in the separate cell culture chambers 213 are disposed in organ chip receiver 204 of organ chip holder 201 in a stacked arrangement. Fluid medium communication channels 215 and cell culture medium reservoirs 202 are positioned in fluid communication. Cell culture medium 212 is delivered to cell culture chambers through first fluid medium communication channel 215.1 or second cell culture medium reservoir 202.2 by alternately rotating body cube 200 clockwise and counter-clockwise with respect to axis of rotation 220.

In an embodiment, a process for determining a pharmacokinetic, a pharmacodynamic, or a pharmacokinetic-pharmacodynamic (PKPD) effect of an agent on a cellular tissue includes providing body cube 200; seeding cellular tissue in cell culture chamber 213 of body organ chip 208, such that the seeded cellular tissue is disposed in cell culture chamber 213 of body barrier chip 207 and first cell culture chamber 213.1 of first body organ chip 208.1 when body organ chip 208 and body barrier chip 207 are stacked body chips 206; and disposing body chips 206 in organ chip receiver 204 of organ chip holder 201. Cell culture medium 212 is provided in first cell culture medium reservoir 202.1 or second cell culture medium reservoir 202.2 of organ chip holder 201. Fluid medium communication channels 215 and cell culture medium reservoirs 202 are positioned in fluid communication. Cell culture medium 212 is delivered to cell culture chambers through first fluid medium communication channel 215.1 or second cell culture medium reservoir 202.2 by alternately rotating body cube 200 clockwise and counter-clockwise with respect to axis of rotation 220. A pharmacokinetic, a pharmacodynamic, or a pharmacokinetic-pharmacodynamic assay is performed on the cellular tissue after delivering cell culture medium 212. One or more in vitro pharmacokinetic or pharmacodynamic effects of the agent on the cellular tissue are determined based on the assay. Multiple body organ chips 208 can be stacked together with different tissues in their cell culture chambers 213 so that such tissues can represent the liver and another organ system, such as the GI tract either in physiological volume ratios or in volume ratios that are not physiological.

Body cube 200 and processes disclosed herein have numerous beneficial uses, including the culture of tissues with near physiological amounts of blood surrogate, the culture of tissues under fluidic flow that is provided on both sides of the tissue without the need for the use of a porous membrane, and the operation as single or multi-organ mircophysiological system without the loss of blood surrogate to the environment. Advantageously, body cube 200 overcomes limitations and technical deficiencies of conventional devices and conventional processes such as tissue chips that contain non-physiological amounts of blood surrogate or liquid, tissue chips that require the use of a porous membrane to provide fluidic flow on both sides of the tissue, and tissue chips that leak fluid to their environment. Further, through its modularity, body cube 200 combines several tissues in non-physiological volume ratios, or in physiological volume ratios for study of drug interactions with the tissues, to aid the discovery of secondary drug metabolite toxicities, and to uncover mechanism in which drugs act on the tissues.

Conventional body-on-a-chip systems designed to mimic the human body that may replace animal models and assist in drug development have not been used in industry. The reasons are that conventional microfluidic systems with many tissue chips and active pumps often leak, are expensive, and are not easy to assemble. Body cube 200 overcomes these issues and is an easy-to-use pumpless gravity-driven article that is modular and expandable. Beneficially, body cube 200 provides an in vitro body mimic with near-physiological amount of a liquid such as a blood surrogate. Conventional systems lack operation with near-physiological liquid levels.

Body cube 200 and processes herein unexpectedly allows for the culture of multiple tissues, wherein the cell culture medium, e.g., blood surrogate, that was in contact with those tissues recombines in cell culture medium reservoirs 202.1 and 202.2 so that any metabolites produced in any of the tissues is mixed with the cell culture medium or blood surrogate arriving from all of the other tissues. Moreover, body cube 200 provides a way to split the fluidic flow of cell culture medium or blood surrogate that flow through the tissue chambers so that the flow through each chamber is the same as the flow of blood would be inside the human or animal body in a tissue size of the same size as provided in tissues 219.1 to 219.n. This process enables the cube to provide metabolites produced in any of the tissues to enter all other tissues at near-physiological concentrations and at near-physiological flow rates.

The articles and processes herein are illustrated further by the following Example, which is non-limiting.

EXAMPLE

Decreasing the amount of liquid inside microphysiological systems (MPS) can help uncover the presence of toxic drug metabolites. However, maintaining near-physiological volume ratios among blood surrogate and multiple organ mimics is technically challenging. This Example describes a body cube and shows its ability to support four human tissues (kidney, GI tract, liver, and bone marrow) scaled down from in vivo functional volumes by a factor of 73,000 with 80 µL of cell culture medium (corresponding to ~1/3000th of in vivo blood volume).

GI tract cells (Caco-2), liver cells (HepG2/C3A), bone marrow cells (Meg-01), and kidney cells (HK-2) were co-cultured inside the body cube with 80 µL of common, recirculating cell culture medium for 72 h. The system was challenged with acetaminophen and troglitazone, and concentrations of aspartate aminotransferase (AST), albumin, and urea were monitored over time. Cell viability analysis showed that 95.5%±3.2% of liver cells, 89.8%±4.7% of bone marrow cells, 82.8%±8.1% of GI tract cells, and 80.1%±11.5% of kidney cells were viable in co-culture for 72 h. Both acetaminophen and troglitazone significantly lowered cell viability in the liver chamber as indicated by viability analysis and a temporary increase of AST in the cell culture medium. Both drugs also lowered urea production in the liver by up to 45%. Cell viability data and the production of urea and albumin indicate that the co-culture of GI tract, liver, bone marrow, and kidney tissues with near-physiological volume ratios of tissues to blood surrogate is possible for up to 72 h. The body-cube was capable of reproducing liver toxicity to HepG2/C3A liver cells via acetaminophen and troglitazone. The body cube provides a viable format for acute toxicity testing with near-physiological blood surrogate to tissue volume ratios.

Drug toxicity testing with microphysiological systems has the potential to replace animal experiments in the drug development process. Microphysiological systems (MPS) are small microfluidic cell-culture devices that house several tissues as well as a recirculating blood surrogate. Adding drugs to the blood surrogate mimics an intravenous drug administration, and once the drug reaches the co-cultured tissues, it is metabolized via the same pathways that convert it into its metabolites and waste products inside the human body.

Microphysiological systems can replicate known metabolic pathways and produce the expected metabolic products. Because both efficacy and toxicity depend on drug metabolite concentration profiles, predicting them with microphysiological systems requires that metabolite concentrations produced with the systems match those produced in the body.

The main strategies to producing in vivo drug concentration profiles with microphysiological systems have been to design the systems so that the ratios of functional units of tissues match those present in vivo, and to employ tissues of high quality with cellular activities that approach in vivo activities. Tissues that approach in vivo cellular activities often consist either of patient-derived primary tissues, or tissues made from stem cells. Both can be expensive and difficult to obtain in large quantities. Microphysiological systems that only represent a small fraction of the human body ($1/100000^{th}$ to $1/50000^{th}$) are best suited for use with such tissues because they require a smaller number of cells to satisfy the functional volume requirement than larger systems. However, in such small systems, the volume of cell culture medium that represents a physiological equivalent of blood is small—60 µL to 300 µL—and microfluidic systems are difficult to operate with such small amounts of recirculating liquid.

In this Example, a microphysiological platform includes chambers for four organs and that can be operated with 80 µL of recirculating cell culture medium. We demonstrate the device with four tissues composed of cells from immortalized cell lines: GI tract epithelial cells (Caco-2), liver cells (HepG2/C3A), bone marrow cells (Meg01), and kidney cells (HK-2). Each tissue was first cultured separately on a 3D scaffold for 24 h, and then the tissues were combined within the device for co-culture. The system supports the co-culture of those tissues for up to 72 h, and recreates acute liver toxicity of acetaminophen and troglitazone. The platform is modular and allows for more tissues to be added in the future. The design has the added advantage of utilizing gravity to drive fluidic flow, making it inexpensive, reliable, and easy to use.

Figure 17:
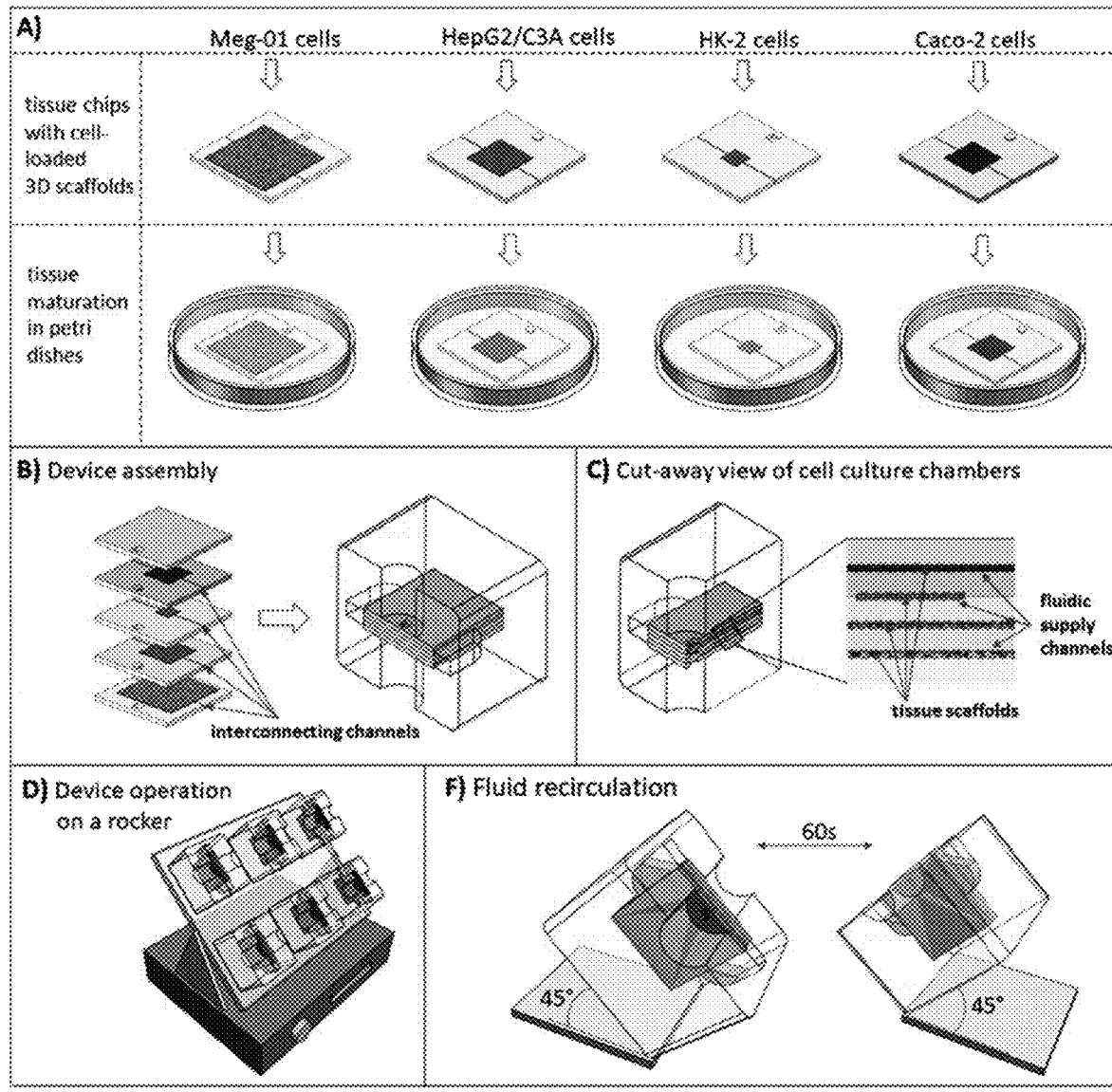
FIG. 17 shows assembly and operation of the body cube according to the Example. A) Maturation of tissues on individual chips: a cell culture scaffold is placed into the tissue chamber of each chip and tissue maturation takes place in separate environments. B) Device assembly: once the tissue matured, the chips are stacked on top of each other and inserted into the cube-shaped holder so that the interconnecting channels line up with the to medium reservoirs. C) Cut-away view of the tissue chips when assembled: each tissue is separated from other tissues, and microfluidic channels on top and below the tissue supply the tissue with recirculating cell culture medium. D) and E) The device is placed on a rocker platform that that periodically tilts by ±45°. The culture medium flows through the upper reservoir through all tissue chips, and recombines in the lower reservoir. The process is then repeated in the other direction.

The system includes a cube-shaped holder that has two medium reservoirs, one on either side, and that can hold four tissue chips (FIG. 17). To assemble the microphysiological system, the four tissue chips are first loaded with cells, then stacked on top of each other, and then inserted into the holder. When the chips are stacked on top of each other, the solid back of each chip effectively closes the tissue chamber and fluidic channels of the chip underneath. Each chip has a set of custom-sized microfluidic channels that connect the tissue chamber with the two reservoirs of the holder. When the holder is tilted at a 45° angle, cell culture medium from one reservoir flows through all tissue chips simultaneously, but at individual flow rates. The flow rates are organ-specific and they are determined by the combined hydraulic resistances of the fluidic channels and the cell culture chamber on each chip. The cell culture medium flows into the second reservoir, where it recombines (FIG. 17). When the holder is tilted by 45° in the other direction, the recombined cell culture medium now flows back through the tissue chips, exposing all tissues to diluted metabolites. The tilting sequence is repeated every sixty seconds, so that toxic metabolites produced in any of the tissues is redistributed among all other tissues.

The system achieves an overall blood surrogate volume of 80 µL. This volume of blood surrogate corresponds to $1173000^{th}$ of the blood volume present in the body of an average person. We designed the cell culture chambers so that they represent $1173000^{th}$ of their in vivo volume. Since blood vessels are represented in our system by microfluidic channels, we subtracted the blood vessel volumes of in vivo organs to obtain the organ volumes that are closer to their actual functional volumes ($V_{functional}$) (Eq. 1). The blood vessel content is given by the blood plasma volume ($V_{plasma}$), the volume of blood cells ($V_{blood\ cells}$), and the volume of endothelial cells ($V_{endothehal\ cells}$). Data for whole organ volumes and blood vessel content were obtained.

$$V_{functional} = V_{organ} - (V_{plasma} + V_{blood\ cells} + V_{endothelial\ cells}) \quad (1)$$

The tissue culture chamber volumes for the cube ($V_{cube}$) were obtained by dividing the calculated in vivo functional organ volumes ($V_{functional}$) by 73000 (scaling factor, SF) (Eq. 2).

$$V_{cube} = V_{organ}/SF \quad (2)$$

To create 3D tissues within each tissue culture chamber, we seeded cells onto scaffolding that was 200 μm thick and 90% porous. Since the scaffold does not contribute to the function of the tissue, but takes up 10% of the chamber, the chamber volumes were increased by 10%. The final tissue chamber sizes are listed in FIG. 15.

Each individual tissue chip contains a set of microfluidic channels that delivers cell culture medium to the tissue chamber. When placed into the holder, the channels line up with the two reservoirs on either side of the chip, forming an interconnected system of tissue chips through which the cell culture medium recirculates (FIG. 17).

The channel sizes were chosen to provide a passive hydraulic resistance that limits medium flow through the chip's tissue chamber to near-physiological values. Calculations of channel sizes were performed. Flow rates were considered near-physiological when they created fluid residence times within each organ chamber that are comparable to blood residence times in the same volume of tissue in the body (FIG. 16).

Blood residence times ($\tau_{phys}$) were calculated using the ratio of blood flow through each organ per time interval ($Q_{in\ vivo}$) and organ volumes ($V_{organ}$) (Eq. 3).

$$\tau_{phys} = V_{organ}/Q_{in\ vivo} \quad (3)$$

We then calculated the needed in vitro flow rate ($Q_{cube}$) using the functional volumes of the cell culture chambers ($V_{cube}$) and the in vivo fluid residence time ($\tau_{phys}$) (Eq. 4).

$$Q_{cube} = V_{cube}/\tau_{phys} \quad (4)$$

The needed hydraulic channel resistances that allow us to achieve near-physiological fluid residence times with gravity-driven medium flow are determined via equations 5 and 6. A channel's needed hydraulic resistance (R) is calculated using the desired flow rate ($Q_{cube}$), and the pressure difference (ΔP) between the two medium reservoirs (Eq.5).

$$R = \Delta P/Q_{cube} \quad (5)$$

To create a pressure difference, we tilt the device at an angle so that the liquid levels between the two reservoirs become different. The resulting pressure difference is calculated using the density of the cell culture medium (ρ), the gravitational constant (g), and the resulting height difference between the liquid levels in the two reservoirs (H) (Eq. 6).

$$\Delta P = \rho g H \quad (6)$$

In addition to the hydraulic resistances of the microfluidic delivery channels, we must also consider the hydraulic resistances provided by the channels inside the cell culture chambers. Within each cell culture chamber, the fluidic stream coming from the delivery channel branches out into a set of parallel channels that are 200 μm wide, 200 μm high, and 200 μm apart from each other. The total hydraulic resistance provided by those channels is calculated using equation 7. Here $R_n$ is the hydraulic resistance of each of the n parallel channels that exist in a given cell culture chamber.

$$\frac{1}{R_{channels\ in\ tissue\ chamber}} = \frac{1}{R_1} + \frac{1}{R_2} + \cdots \frac{1}{R_n} \quad (7)$$

The heights and widths of the microfluidic delivery channels can be accurately controlled with microfabrication techniques. The opportunity to adjust those dimensions allows us to create customized hydraulic resistances for each cell culture chamber (Eq. 8). For channels with rectangular cross-sectional shapes, equation 8 relates channel height and width to their hydraulic resistance. We adjust the height and width of each channel to achieve the hydraulic resistance needed to create the desired flow rate ($Q_{cube}$) in the tissue chamber.

$$R_{channels} = \frac{12\eta L}{wh^3} * \left[1 - \frac{192h}{\pi^5 w}\tanh\left(\frac{\pi w}{2h}\right)\right]^{-1} \quad (8)$$

In equation 8, η is the kinetic viscosity of the medium, L is a length of the channel, h is the height of the channel, and w is the channel's width. The calculated and actual organ chamber and channel sizes are listed in FIG. 23.

The cube holder and all tissue chips were designed using 3D drawing software. Each tissue chip measured 20 mm×20 mm×1 mm. The tissue culture chambers were designed as 200 μm deep, square cavities with lengths and widths listed in table 1. The microfluidic channels on the tissue chips were all 200 μm deep, but of varying lengths and widths. The lengths and widths are listed in table 2. The holder and the tissue chips were all 3D-printed by a commercial vendor using a high-resolution material. The printed tissue chips as well as the chip holder were then coated with a 1 μm thick layer of parylene C. To build the final four-organ system the chips are loaded with cells, stacked against each other, and placed into the cube holder (FIG. 17).

HepG2/C3A cells (ATCC) were cultured using Eagle's Minimum Essential Medium (EMEM) with 50 mL fetal bovine serum. Caco-2 cells were cultured using an Eagle's Minimum Essential Medium with 100 mL fetal bovine serum. MEG-01 cells were cultured using ATCC-formulated RPMI-1640 medium with 50 mL fetal bovine serum. HK-2 cells were cultured using formulated RPMI-1640 medium with 50 mL fetal bovine serum. All cells were maintained at 37° C., with a volume gas fraction of 5% $CO_2$. Once confluent, the cells were detached from the cell culture flask with trypsin (trypsin-EDTA, 0.25% volume fraction), and separated from the medium by centrifugation.

Tissue culture scaffolds designed for 3D cell culture were used. The scaffolds are 200 μm thick, porous, cross-linked polystyrene sheets with an average void size of 42 μm. The scaffolds were loaded with either Caco-2, HepG2/C3A, MEG-01, or HK-2 cells at the following densities: Caco-2: 279×10³ cells per scaffold (10% of physiologic density), HepG2/C3A: 45×10³ cells per scaffold (20% of physiologic density), MEG-01: 2000×10³ cells per scaffold (20% of physiologic density), HK-2: 12.7×10³ cells per scaffold (10% of physiologic density). The cell-loaded scaffolds were placed into petri dishes and the cells were maintained for 24 h at 37° C., with a volume fraction of 5% $CO_2$, using culture medium appropriate for each cell type.

After 24 h, the cell-loaded 3D scaffolds were aseptically transferred into the tissue chambers of the appropriate tissues chip. The chips were then placed on top of each other, so that the back of one tissue chamber closed the opening of the tissue chip below it. The tissue chip stack was then inserted into the holder. The two reservoirs of the cube were filled with 32.5 µL of EMEM (containing a volume fraction of 10% FBS) each, and the device was placed onto a rocker platform that tilted back and forth at an angle of 45°. The platform changed its tilt from 45° to −45° every 60 s continuously for 72 h. Culture medium was collected and replaced with fresh medium after 1 h, 16 h, 24 h, 40 h, 48 h, and 64 h. The total amount of blood surrogate (i.e. the amount of cell culture medium that we consider blood surrogate) inside the system consisted of 2×32.5 µL (medium in the reservoirs), plus 15 µL (medium inside the microfluidic channels that deliver medium to the tissue culture chambers).

After 72 h of operation, the cube was disassembled, and the cells on the scaffolds were stained with viability stain.

Urea concentrations were measured in the collected cell culture medium using an appropriate assay kit. To conduct the measurement, 5 µL of the collected medium were transferred into the wells of a 96-well plate, and 200 µL of the working reagent was added. The plate was tapped lightly to mix medium and reagents. After 50 min of incubation at room temperature in the dark, the working reagent formed a coloured complex specifically with urea. The absorbance of the coloured complex was measured at 430 nm using a plate reader. The results were obtained from the standard curve and expressed as µg per million cells produced in relation to a 1 h baseline measurement.

Albumin synthesis was evaluated by ELISA (enzyme-linked immunosorbent assay), using a kit and following the manufacturer's directions. In short, the 96-well plate was coated with goat anti-human albumin antibody and the wells washed with buffer. Diluted samples and standards were added into the coated wells. After incubation, the wells were washed with buffer, horse radish peroxidase-conjugated goat anti-human antibody was added and incubated for 1 h. Following another wash step, 100 µL of enzyme substrate (tetramethylbenzidine) were added and incubated for 15 min. The reaction was stopped by adding 100 µL stop solution. Plate was measured at 450 nm using a plate reader. The results are expressed as µg per million cells produced in relation to a 1 h baseline measurement.

To estimate cell death during co-culture, we measured AST concentrations in the cell culture medium recovered from the devices after 1 h, 16 h, 40 h and 64 h of co-culture. The AST activity was measured with an assay kit. Briefly, standard samples and medium samples were added to the 96 well plate. We then added 100 µL of working solution to each well and mixed both solutions by gently tapping the plate. The plate was then incubated inside a plate reader in the dark, at 37° C. After 5 min of incubation, the absorbance at 450 nm was measured, and the measurement was repeated every 5 minutes until absorbance of the most active sample exceeded the standard curve's largest absorbance. We then selected the initial absorbance value inside the linear range and calculated the AST concentrations using the protocol given in the kit. The results are expressed as µg per million cells produced in relation to a 1 h baseline measurement.

The cell number in each tissue culture scaffold before culture on the chip was measured by HS cell viability reagent. Briefly, the standard curve of each cell line was obtained by seeding predetermined numbers of cells (counted by an automated cell counter) into 6 well plates and measured the fluorescence of incubated culture medium (ex/em is 560/590). The cell numbers on the seeding scaffold was measured following a similar procedure by incubation with alamar blue reagent and measurement of the incubated culture medium. After co-culture experiments, cell viability was determined by cell viability stain.

To determine the volume flow rate, we added 5 µL EBM-2 with growth factor to the bottom reservoir, then 65 µL of EBM-2 with growth factor to the top reservoir. We then let the medium flow through the device for thirty seconds. The culture medium in the bottom reservoir was collected and weighed. The volume change of culture medium in the bottom reservoir and volume flow rate was calculated. Then the flow rate was adjusted to account for the viscosity difference at room temperature and 37° C.

We simulated the fluidic flow inside the body cube using a method we described earlier. In short, 3D software models of the tissue chambers were imported into COMSOL 5.5. Stationary total flow rates in the device under 6 different liquid level differences were simulated in COMSOL. The correlation of the liquid level differences and total flow rate was determined by polynomial regression curve fitting. Then one partial differential equation (PDE) for the total flow rate in the device was built based on the liquid level difference versus flow rate fitting curve, and another PDE for the angular position of the device was built based on the motion of the rocking platform. Those PDEs were solved with MATLAB PDE solver ode45 with absolute tolerance $10^{-10}$ and a relative tolerance $10^{-7}$ in MATLAB R2016b. Since the ratios of flow rate in each organ chamber were equal to the ratios of the reciprocal of their hydraulic resistances, the flow rate in each chamber could be calculated.

To accommodate four tissues with 80 µL of recirculating cell culture medium, we designed a cube-shaped holder that held a total of four tissue chips (FIG. 17). Stacking the chips allowed us to shorten the interconnects and with that the amount of liquid needed to operate the device. Medium flow across the tissues was achieved via channels that were etched into the tissue culture chamber lids, i.e. the back of each adjacent tissue chip. The channels were 200 µm wide on a 400 µm pitch.

Figure 18:
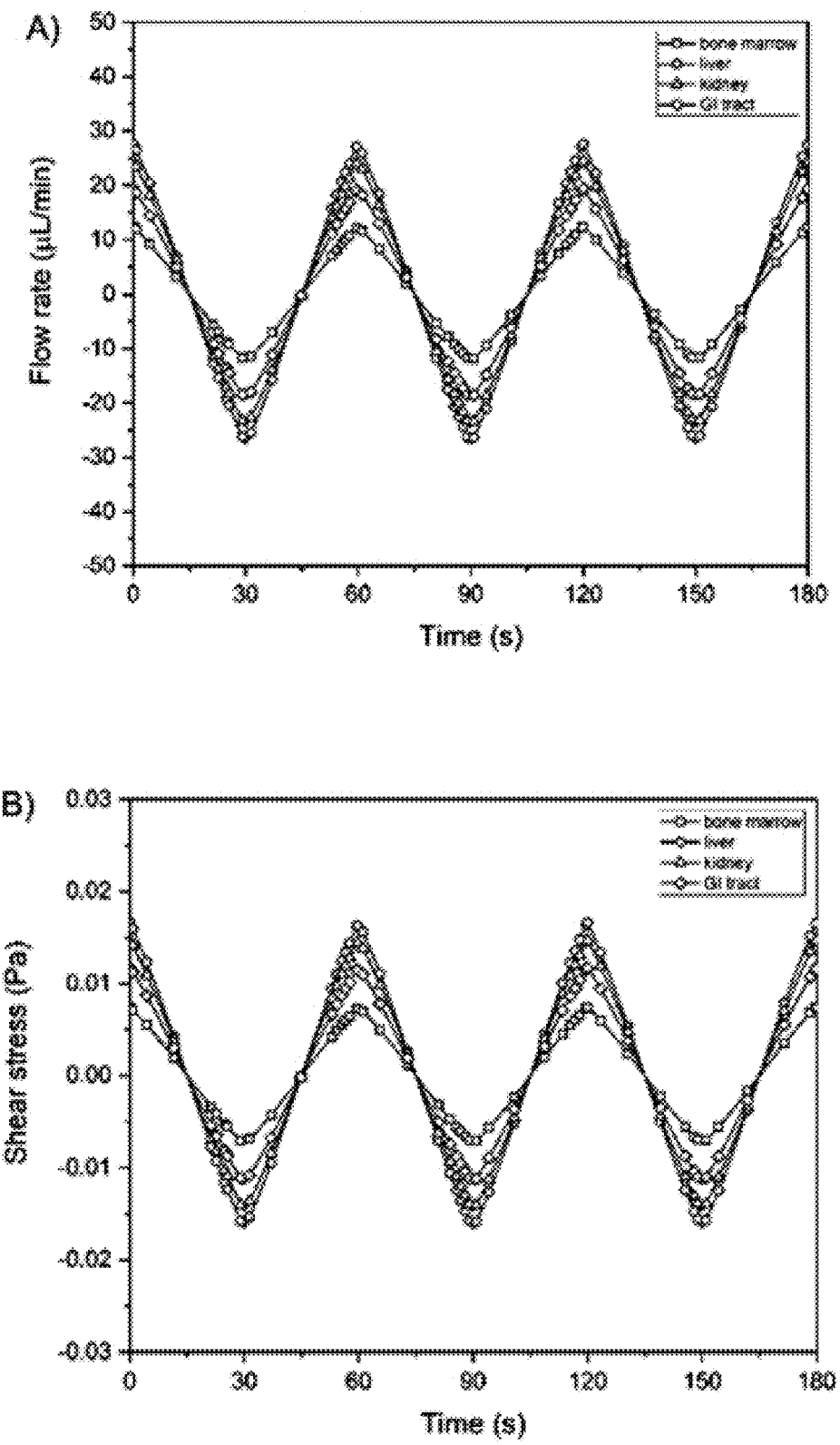
FIG. 18 shows simulated flow rates (A) and shear forces (B) inside the tissue chambers of the body cube according to the Example.

The amount of recirculating cell culture medium inside the body cube consisted of three fractions. The combined amount of cell culture medium in the two reservoirs was 65 at any given time, while the amount of cell culture medium inside the network of fluidic channels was 15 µL. The system also contained a small amount of cell culture medium that resided in each tissue culture chamber and filled the space not occupied by either cells or scaffold. The total flow rate measured was 3.36 µL/s±0.40 µL/s. The flow in each tissue culture chamber was simulated computationally and is shown in FIG. 18. The flow rate periodically increases and then reverses direction as the device is rocked back and forth. The average flow rates were 11.0±0.1 µL/min (GI tract), 15.6±0.1 µL/min (liver), 13.8±0.1 µL/min (kidney), and 7.0±0.1 µL/min (bone marrow).

Figure 20:
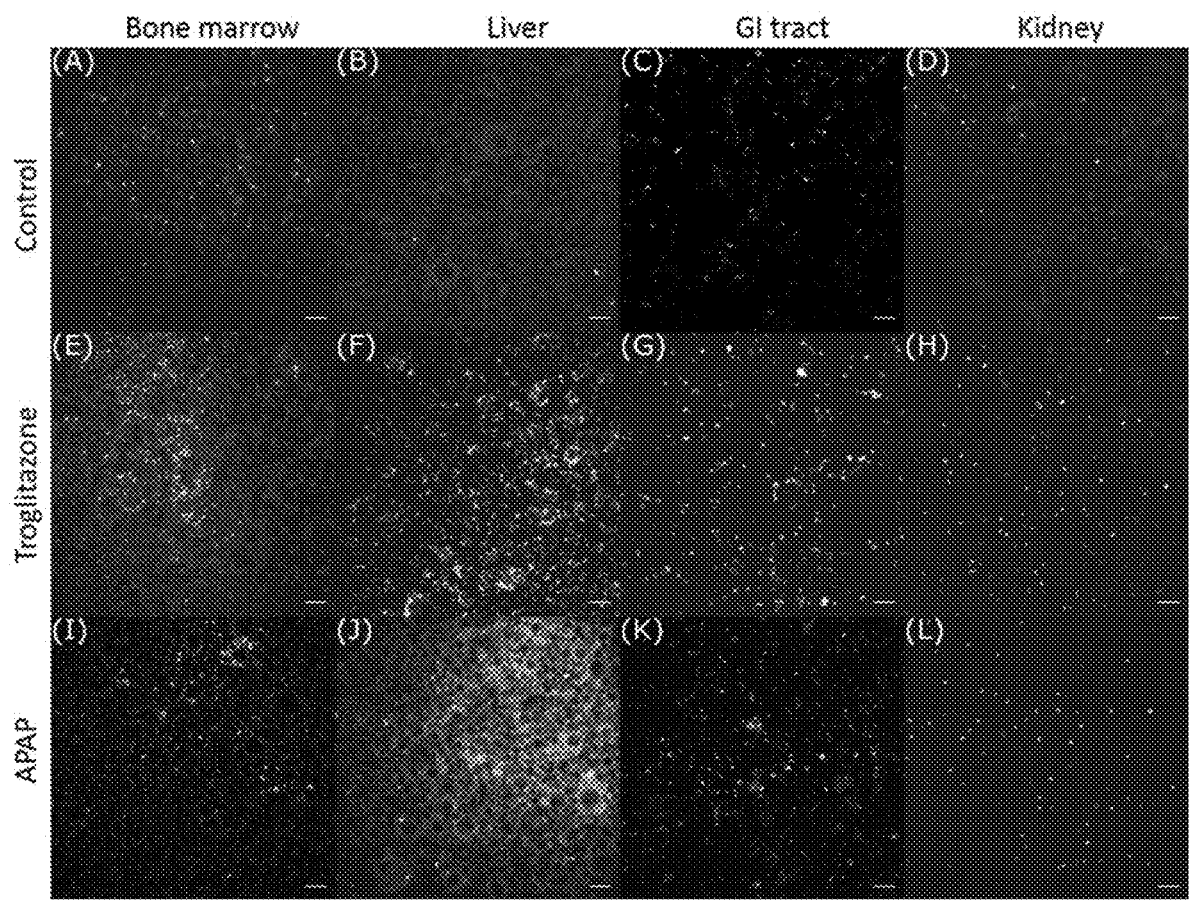
FIG. 20 shows fluorescence microscopy images of cells co-cultured in the body cube for 72 h according to the Example. Control cultures without drug: (A) bone marrow, (B) liver, (C) GI tract, (D) kidney. Co-cultures exposed to troglitazone: (E) bone marrow, (F) liver, (G) GI tract, (H) kidney. Co-cultures exposed to acetaminophen (APAP): (I) bone marrow, (J) liver, (K) GI tract, (L) kidney. The cells were stained with viability dye. Blue cells are live cells and pink cells are no longer viable. Scale bars represent 100 μm.
Figure 21:
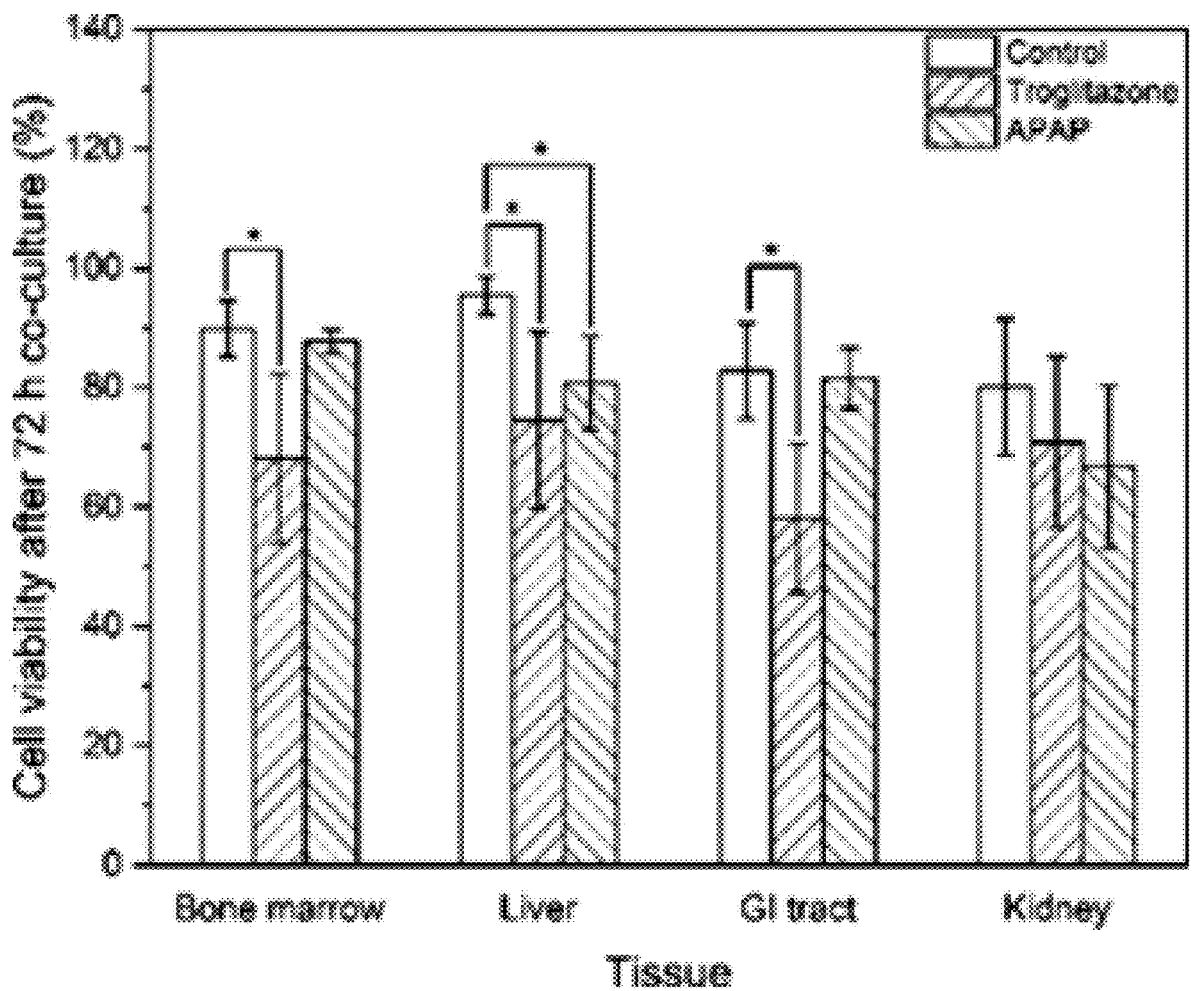
FIG. 21 shows percentage of bone marrow, liver, GI tract, and kidney cells that are viable after three days of co-culture with medium recirculation in the body-cube device according to the Example. Column heights represent means of n≥3 experiments, and error bars represent±standard deviations.

We recovered all tissue scaffolds from the cube after 72 h of co-culture, stained the cells with viability dyes, and imaged the cells via fluorescence microscopy (FIG. 20). The images show that the scaffolds recovered from all four tissue chambers are populated with live cells as well as a smaller fraction of dead cells. Bone marrow and liver cells were most amenable to 72 h of co-culture in the low-liquid environment. Image analysis showed that 95.5%±3.2% of liver cells, and 89.8%±4.7% of bone marrow cells were still viable after the recovery (FIG. 21). The numbers of live cells after 72 h of operation were lower in the GI tract tissue (82.8%±8.1%) and the kidney tissue (80.1%±11.5%) (FIG. 21).

To measure the production and secretion of albumin and urea into the cell culture medium, we used a portion of the cell culture medium recovered from the devices every day. On the first day of culture, the medium albumin content was 0.74 µg±0.11 µg per day per million cells, with lower concentrations measured on days two (0.55 µg±0.13 µg per day per million cells) and three (0.31 µg±0.04 µg per day per million cells). Similarly, the urea content in the cell culture medium was 72.1 µg±6.0 µg per day per million cells on the first day, and lower on days two (64.6 µg±9.8 µg per day per million cells) and three (53.4 µg±10.5 µg per day per million cells) of co-culture.

Figure 22:
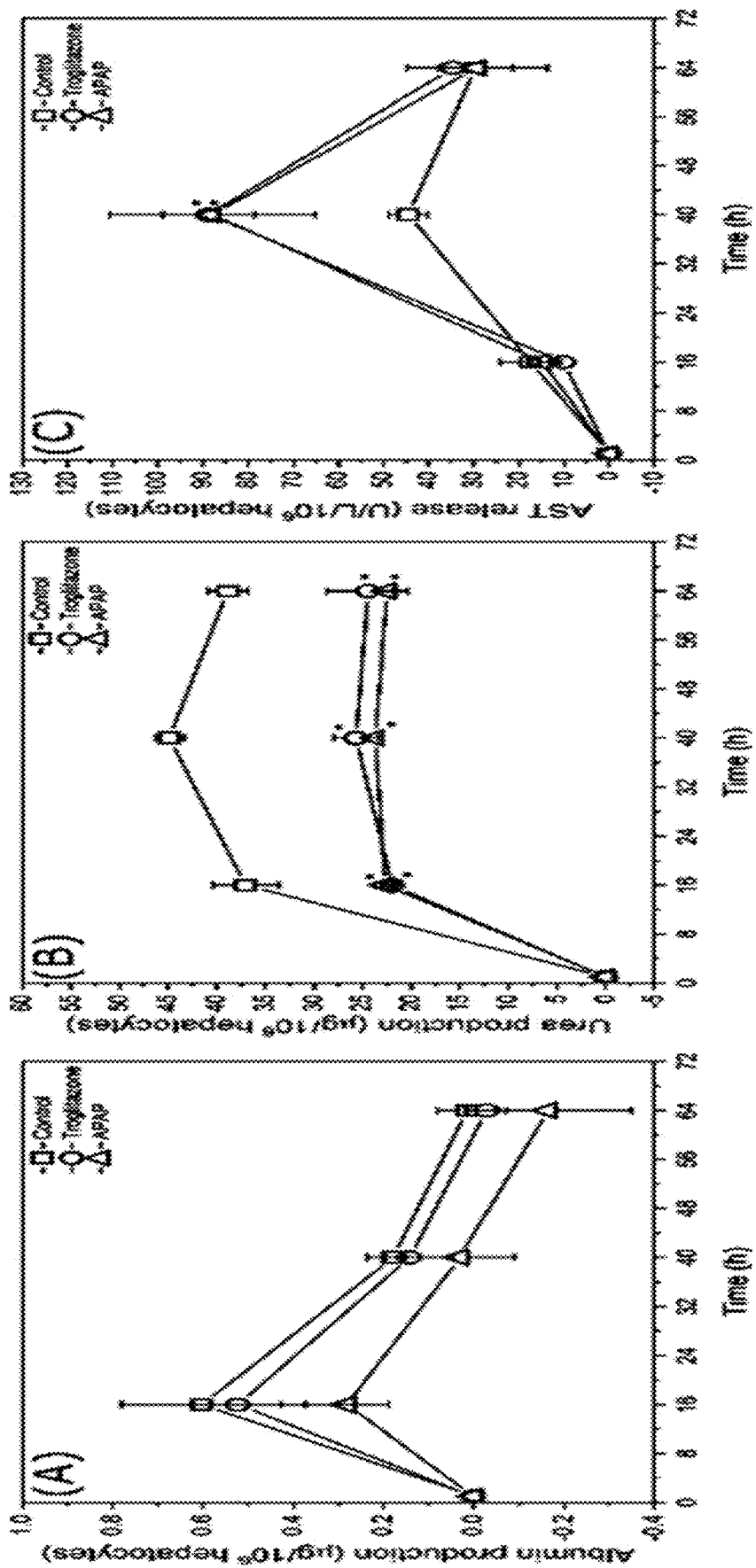
FIG. 22 shows changes in reference to the 1 h timepoint in production of albumin (A) and urea (B) produced by HepG2/C3A liver cells when cultured together with bone marrow, GI tract and kidney cells inside the body-cube for three days according to the Example. Data points represent means of n≥3 experiments, and error bars represent ±standard deviations.

To determine whether the body cube can detect acute cellular toxicity, we challenged the device with two toxins that are known to cause damage to liver HepG2 cells when exposed at high concentrations, acetaminophen, and troglitazone. Similar to the baseline experiments described above, we recovered cell cultures after 72 h of co-culture from the device. Fluorescence images confirm that both acetaminophen and troglitazone cause significant liver damage when compared to control conditions without drug (FIG. 21). This result is confirmed by the differences in AST released from cells cultures treated with acetaminophen and troglitazone. Compared to control conditions without drug, the amount of AST in the cell culture medium is significantly higher, indicating significant liver cell death. In addition, urea production, but not albumin production was decreased when drugs were added to the cube (FIG. 22).

The microphysiologic system can be operated with small amounts of cell culture medium, so that the volume of blood surrogate in the system is close to physiological values. We calculated on-chip organ volumes and on-chip blood surrogate content using data for a 70 kg male human and normalized data to a 70 kg human by scaling the values assuming a directly proportional relationship. Because organs contain varying amounts of vasculature, and the in vitro tissues we constructed here do not (the blood vessels are moved to the outside of the tissue and are mimicked by the fluidic channels that supply cell culture medium to the tissues), we removed the volumes of vascular endothelial cells and blood volumes from the overall reported organ volume to obtain a volume that is closer to its functional volume. The amount of blood surrogate volume (80 µL) was calculated using the same scaling factor (73000) as for the organs. Our method to calculate functional organ volumes is only a first approach to creating microphysiological systems.

To operate the MPS with only physiological amounts of cell culture medium (80 µL), we designed the system in a cube format where the tissue chips are stacked on top of each other, and fluidic connections among organ chambers are short. In addition, using gravity to drive fluidic flow allowed us to eliminate tubing and connections typically used with peristaltic pumps, and with that to decrease the amount of liquid needed to operate the system.

The device we developed here is modular, meaning that all tissue chips can be handled separate from each other during the time of cell seeding. Tissue maturation can take place in separate dishes with cell culture medium customized for each cell type. Each chip also contains channels with tissue-specific dimensions that provide the connection to the main reservoirs. This feature allows us to quickly adjust the overall system by switching organ chips, and adding new ones when needed.

Physiological amounts of blood surrogate (cell culture medium) in a microphysiological system are relatively small amounts of liquid for conventional microfluidic system, making it difficult to recirculate it. In the MPS presented here, all organ compartments were scaled by a factor of 73000, and the corresponding physiological amount of blood surrogate is 80 µL of cell culture medium. This Example demonstrates an MPS design that can recirculate such small amounts of cell culture medium.

To operate the MPS with 80 µL of cell culture medium, we designed it as a cube. In the cube, interconnecting channels needed to recirculate the liquid among all cell culture chambers re short, allowing us to stay within the 80 µL limit. All conventional microphysiological systems have a 2D layout, where organ chambers are arranged next to each other on a 2D plane. The channels interconnecting organ chambers with each other and with medium reservoirs are long and require additional liquid volumes that push the amount of blood surrogate within the system beyond what would be physiological.

An alternative strategy to achieve physiological amounts of blood surrogate in an MPS is to scale the organ chambers in the device less aggressively using a smaller scaling factor. The overall volumes of tissues and blood surrogate would increase, making it easier to operate and handle the MPS. However, in order to retain physiological tissue cell densities, that strategy would require the use of larger numbers of cells to construct each tissue. When using patient-derived primary cells, using larger numbers of cells may become prohibitively expensive. Choosing scaling factors between 60000 to 100000 are likely the most useful, because the resulting cell culture chambers can be filled with in vitro tissue constructs containing less than a million cells. At the same time the blood surrogate volume would still within a range that can be recirculated (60 µL to 100 µL).

In general, another approach to achieving physiological liquid volumes in MPS is to eliminate tissue chambers for tissues that are known to not interact with the drug from the system. Such tissues would neither absorb, redistribute, or convert the drug, or be otherwise affected by it. When this is the case, the chamber for that organ can be eliminated along with the accompanying fluidic channels, decreasing the amount of liquid needed inside the MPS.

Despite containing physiological amounts of blood surrogate, the overall liquid-to-cell ratio in our device is still not fully physiological. This is in large part due to the tissue's cell densities that range between 10% to 20% of in vivo values (FIG. 19). Similar to the tissues in the human body, the spaces in each organ chamber that are not occupied by either cells or scaffold, are also filled with cell culture medium. The amount of that interstitial liquid, i.e., the liquid between cells, can also significantly contribute to the dilution of drug metabolites. When using in vitro cell cultures, attention must be paid to the density of cells achieved within the tissue construct. In vitro tissues tend to be much less densely populated with cells than in vivo tissues. That means the amount of interstitial liquid is higher than it would be in the body. While the cell density within the tissue construct we used was still far from physiological values (10% to 20%), future developments of 3D scaffolds that allow for higher cell densities will help eliminate non-physiological amounts of interstitial liquid.

Our device contained 80 µL of liquid, and supported four tissues for three days. Fluorescent images of scaffolds with cells recovered from the cube after 72 h of operation were evaluated and confirm that the majority of cells were viable in all cell culture chambers. Some cells (5% to 20%, depending on the tissues) were no longer viable.

Liver cells also produced albumin and urea with values showing a downward trend at the 72 h timepoint. A 24 h to 72 h timeframe is suitable for detecting acute drug toxicity, but chronic effects require longer co-culture times to manifest.

To achieve co-culture times that are longer than three days, additional strategies to maintain the cultures with low levels of liquid need to be developed. First, evaporation of liquid must be limited. While using our body-cube we noticed that a significant amount of cell culture medium (about 10%) evaporated from the system per day. This decrease in liquid levels is a consequence of operating the system with gravity, which means the system is not fully closed and cell culture medium is exposed to the incubator environment. That exposure enables necessary gas exchange, but also permits evaporation. When a significant amount of cell culture medium evaporates, concentrations of cellular waste products increase, which could affect cell viability. Future systems should incorporate features that limit evaporation.

To limit the effects of evaporation, we replaced the entire cell culture medium every eight to sixteen hours, a practice that allowed us to replace evaporated medium, as well as remove waste products. However, replacing the cell culture medium every day influences the concentration profiles of any added drugs, as well as those of drug metabolites. Instead of replacing the medium, it can be preferable to include a mechanism that allows for waste removal in another way. A functioning kidney tissue would serve that purpose and likely also increase the time cells are viable. We believe that without such a mechanism the usefulness of microphysiological devices will be limited to evaluating the effects of only acute 24 h drug exposures.

An additional consideration that could allow the cube to achieve longer cell culture times is to improve the composition of the cell culture medium. Here, we used a composition that consisted of equal parts of cell culture medium optimized for each of the four cell types. A custom formulation designed specifically to support all four tissues at the same time could help limit the detrimental effects of limited availability of specific nutrients or growth factors.

To demonstrate that the body cube is capable of measuring drug induced liver injury, we challenged the device with two drugs that are known to cause liver cell toxicity in both primary cells and HepG2 cells (acetaminophen) and in HepG2 cells only (troglitazone). Both drugs caused the expected cell death, and in part due to the decrease in cell number, we also observed an accompanying decrease in metabolic activity of the tissues. Similarly, cytosolic enzymes are released in significantly larger amounts from cell cultures challenged with both drugs than those that were not exposed to drugs after 40 h of exposure. After 48 h the amount of cytosolic enzyme concentration in the medium is similar for both drug-exposed cultures and control cultures. The downward trend in drug-exposed cultures after 40 h is likely due to the fact that a large number of the most sensitive cells were already damaged. On the other hand, the upward trend in control cultures is likely due to the limit in culture time in the cube. The result highlights the need to lengthen the time of tissue viability in the cube. In addition, to detect liver cell toxicity of troglitazone to primary liver cells can be included in 3D tissues of primary liver cells in combination with other non-parenchymal liver cells.

The body cube is a multi-organ microphysiological device that can be operated with small, near-physiological amounts of blood surrogate (cell culture medium). Cells of four tissues, cultured in the cube for three days, were viable and functional, indicating that the cube can be used to test for the toxicity drugs and its metabolites during an acute 24 h to 72 h drug exposure. The developed cube is modular, and was operated with gravity-induced flow, making it easy to use, and attractive for large-scale drug toxicity studies.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix (s) as used herein is intended to include both the singular and the plural of the term that it modifies, thereby including at least one of that term (e.g., the colorant(s) includes at least one colorants). Option, optional, or optionally means that the subsequently described event or circumstance can or cannot occur, and that the description includes instances where the event occurs and instances where it does not. As used herein, combination is inclusive of blends, mixtures, alloys, reaction products, collection of elements, and the like.

As used herein, a combination thereof refers to a combination comprising at least one of the named constituents, components, compounds, or elements, optionally together with one or more of the same class of constituents, components, compounds, or elements.

All references are incorporated herein by reference.

The use of the terms "a," "an," and "the" and similar referents in the context of describing the invention (especially in the context of the following claims) are to be construed to cover both the singular and the plural, unless otherwise indicated herein or clearly contradicted by context. It can further be noted that the terms first, second, primary, secondary, and the like herein do not denote any order, quantity, or importance, but rather are used to distinguish one element from another. It will also be understood that, although the terms first, second, etc. are, in some instances, used herein to describe various elements, these elements should not be limited by these terms. For example, a first current could be termed a second current, and, similarly, a second current could be termed a first current, without departing from the scope of the various described embodiments. The first current and the second current are both currents, but they are not the same condition unless explicitly stated as such.

The modifier about used in connection with a quantity is inclusive of the stated value and has the meaning dictated by the context (e.g., it includes the degree of error associated with measurement of the particular quantity). The conjunction or is used to link objects of a list or alternatives and is not disjunctive; rather the elements can be used separately or can be combined together under appropriate circumstances.

What is claimed is:

1. A body cube for culturing tissue, the body cube comprising:
    an organ chip holder comprising: a first cell culture medium reservoir bounded by a first reservoir wall and that receives a cell culture medium; and an organ chip receiver bounded by a receiver wall and that receives a body barrier chip and a first body organ chip;

the body barrier chip is in mechanical engagement with the receiver wall so that the body barrier chip rotates with the body cube;

the first body organ chip is in mechanical engagement with the receiver wall and the body barrier chip so that the body barrier chip, the first body organ chip, and the organ chip holder rotate together in response to rotation of the body cube, the first body organ chip comprising:
a body chip frame that mechanically engages the body barrier chip and the receiver wall;
a first fluid medium communication channel in fluid communication with the first cell culture medium reservoir and that: is disposed in the body chip frame; and receives the cell culture medium from the first cell culture medium reservoir, wherein a first cell culture chamber is bounded by the body chip frame, is in fluid communication with the first fluid medium communication channel, and receives the cell culture medium from the first fluid medium communication channel in response to rotation of the body cube; and
a second fluid medium communication channel in fluid communication with the first cell culture chamber and that: is disposed in the body chip frame; and receives the cell culture medium from the first cell culture chamber in response to rotation of the body cube; and the body barrier chip and the first body organ chip disposed in the organ chip holder, the first body organ chip comprising: the first cell culture chamber that receives the cell culture medium and produces a first tissue in the first cell culture chamber; and a primary tissue surface on which is disposed the first fluid medium communication channel, the second fluid medium communication channel, and the first cell culture chamber, such that the organ chip holder receives the cell culture medium and communicates the cell culture medium to the first cell culture chamber of the first body organ chip in response to rotation of the organ chip holder, wherein the first cell culture chamber comprises:
a chamber wall that contacts the cell culture medium;
a chamber protrusion disposed on the chamber wall and that protrudes from the chamber wall; and
a chamber flow channel bounded by the chamber wall and the chamber protrusion and that receives the cell culture medium from the first fluid medium communication channel and communicates the cell culture medium through cell culture chamber in which tissue grows to the second fluid medium communication channel.

2. The body cube of claim 1, wherein the body barrier chip comprises:
a body chip frame comprising:
a barrier surface that mechanically engages the receiver wall; and
a secondary tissue surface opposite the barrier surface and that engages the primary tissue surface of the first body organ chip; and
an alignment member disposed on the secondary tissue surface of the body chip frame and that mechanically engages an alignment member on the primary tissue surface of the first body organ chip.

3. The body cube of claim 2, wherein the body barrier chip further comprises a cell culture chamber disposed on the secondary tissue surface.

4. The body cube of claim 3, wherein the cell culture chamber of the body barrier chip comprises:
a chamber wall that contacts the cell culture medium;
a chamber protrusion disposed on the chamber wall and that protrudes from the chamber wall; and
a chamber flow channel bounded by the chamber wall and the chamber protrusion and that receives the cell culture medium from the first fluid medium communication channel of the first body organ chip and communicates the cell culture medium to the second fluid medium communication channel of the first body organ chip and in which the first tissue grows in the cell culture chamber of the body barrier chip and the first cell culture chamber of the first body organ chip.

5. The body cube of claim 4, wherein the first body organ chip further comprises a secondary tissue surface opposite the primary tissue surface of the first body organ chip; and
a second cell culture chamber disposed on the secondary tissue surface of the first body organ chip.

6. The body cube of claim 5, wherein the second cell culture chamber disposed on the secondary tissue surface of the first body organ chip comprises:
a chamber wall;
a chamber protrusion disposed on the chamber wall and that protrudes from the chamber wall; and
a chamber flow channel bounded by the chamber wall and the chamber protrusion.

7. The body cube of claim 6, wherein the first body organ chip further comprises an alignment member disposed on the secondary tissue surface.

8. The body cube of claim 7, further comprising a second body organ chip disposed in the organ chip receiver and in mechanical engagement with the receiver wall and the first body organ chip, such that the body barrier chip, the first body organ chip, the second body organ chip, and the organ chip holder rotate together in response to rotation of the body cube,
wherein the first body organ chip is interposed between the body barrier chip and the second body organ chip.

9. The body cube of claim 8, wherein the second body organ chip comprises a first cell culture chamber opposing the second cell culture chamber of the first body organ chip, such that the first cell culture chamber of the second body organ chip and the second cell culture chamber of the first body organ chip in combination receive the cell culture medium and produce a second tissue in the first cell culture chamber of the second body organ chip and the second cell culture chamber of the first body organ chip, and
the organ chip holder communicates the cell culture medium to the first cell culture chamber of the second body organ chip and the second cell culture chamber of the first body organ chip in response to rotation of the organ chip holder.

10. The body cube of claim 9, wherein the second body organ chip comprises:
a body chip frame that mechanically engages the first body organ chip and the receiver wall;
a first fluid medium communication channel in fluid communication with the first cell culture medium reservoir and that:
is disposed in the body chip frame; and
receives the cell culture medium from the first cell culture medium reservoir,
wherein the first cell culture chamber of the second body organ chip is bounded by the body chip frame of the second body organ chip, is in fluid communication with the first fluid medium communication channel, and receives the cell culture medium from the first cell culture medium reservoir in response to rotation of the body cube; and a second fluid medium communication channel in fluid communication with the first cell culture chamber of the second body organ chip and that:
is disposed in the body chip frame of the second body organ chip; and
receives the cell culture medium from the first cell culture chamber of the second body organ chip in response to rotation of the body cube.

11. The body cube of claim 10, wherein the second body organ chip further comprises:
a primary tissue surface on which is disposed the first fluid medium communication channel, the second fluid medium communication channel, and the first cell culture chamber of the second body organ chip.

12. The body cube of claim 11, wherein the first cell culture chamber of the second body organ chip comprises:
a chamber wall that contacts the cell culture medium;
a chamber protrusion disposed on the chamber wall and that protrudes from the chamber wall; and
a chamber flow channel bounded by the chamber wall and the chamber protrusion and that receives the cell culture medium from the first fluid medium communication channel of the second body organ chip and communicates the cell culture medium to the second fluid medium communication channel of the second body organ chip and in which the second tissue grows.

13. The body cube of claim 1, further comprising a pump that provides the cell culture medium to a cell culture medium reservoir of the organ chip holder for communication of the cell culture medium to the first cell culture chamber of the first body organ chip.

14. A body cube for culturing tissue, the body cube comprising:
an organ chip holder comprising:
an organ chip receiver bounded by a receiver wall and that:
receives a plurality of body chips and a cell culture medium; and
communicates to the body chips a volume of the cell culture medium that is limited to a near-physiological amount of the cell culture medium for growing tissue;
a first cell culture medium reservoir bounded by a first reservoir wall and in fluid communication with the body chips and that receives the cell culture medium and communicates the cell culture medium to the body chips; and
a second cell culture medium reservoir bounded by a second reservoir wall and in fluid communication with the body chips and that receives the cell culture medium from the body chips in response to rotation of the organ chip holder; and
the body organ chips disposed in the organ chip receiver, such that body organ chips are mechanically engaged by the receiver wall so that body chips rotate with the organ chip holder when the organ chip holder is subjected to rotation, and the body chips comprise:

a first body organ chip comprising:
a first body chip frame;
a first fluid medium communication channel disposed in the first body chip frame and in fluid communication with the first cell culture medium reservoir, such that the first fluid medium communication channel receives the cell culture medium from the first cell culture medium reservoir and communicates the cell culture medium to a first cell culture chamber;
the first cell culture chamber disposed in the first body chip frame and in fluid communication with the first fluid medium communication channel, such that the first cell culture chamber:
receives the cell culture medium from the first fluid medium communication channel in response to rotation of the organ chip holder, such that a volume of the cell culture medium accommodated by the first cell culture chamber is limited to a near-physiological amount of the cell culture medium;
produces a first tissue disposed in the first cell culture chamber; and
provides contact between the first tissue and the cell culture medium; and
communicates the cell culture medium to a second fluid medium communication channel; and
a second fluid medium communication channel disposed in the first body chip frame and in fluid communication with the first cell culture chamber and that receives the cell culture medium from the first cell culture chamber in response to rotation of the organ chip holder; and
a body barrier chip in mechanical engagement with the receiver wall and the first body organ chip by an alignment member, the body barrier chip comprising:
a body chip frame;
an alignment member disposed in the body chip frame to mechanically engage the first body organ chip; and
a cell culture chamber bounded by the body chip frame and opposing the first cell culture chamber of the first body organ chip, wherein the first tissue grows between the cell culture chamber of the body barrier chip and the first cell culture chamber of the first body organ chip,
wherein the first cell culture chamber comprises:
a chamber wall that contracts the cell culture medium;
a chamber protrusion disposed on the chamber wall and that protrudes from the chamber wall; and
a chamber flow channel bounded by the chamber wall and the chamber protrusion and that receives the cell culture medium from the first fluid medium communication channel and communicates the cell culture medium through cell culture chamber in which tissue grows to the second fluid medium communication channel.

* * * * *